(12) United States Patent
Joslyn et al.

(10) Patent No.: US 11,579,054 B2
(45) Date of Patent: Feb. 14, 2023

(54) EXTRACTION SYSTEM FOR TESTING MICROBIAL CONTAMINATION OF TISSUE PRODUCTS

(71) Applicant: AlloSource, Centennial, CO (US)

(72) Inventors: Arthur Joslyn, Centennial, CO (US); Kenneth Blood, Littleton, CO (US); Jan Zajdowicz, Aurora, CO (US); Lauren Kapushion, Erie, CO (US); Amy Kippen, Fort Collins, CO (US); Samantha White, Highlands Ranch, CO (US); Donald White, Fort Collins, CO (US)

(73) Assignee: ALLOSOURCE, Centennial, CO (US)

( * ) Notice: Subject to any disclaimer, the term of this patent is extended or adjusted under 35 U.S.C. 154(b) by 979 days.

(21) Appl. No.: 16/381,531

(22) Filed: Apr. 11, 2019

(65) Prior Publication Data

US 2019/0316997 A1 Oct. 17, 2019

Related U.S. Application Data

(60) Provisional application No. 62/656,254, filed on Apr. 11, 2018.

(51) Int. Cl.
*G01N 1/40* (2006.01)
*B01J 19/10* (2006.01)
*C12Q 1/00* (2006.01)
*G01N 1/08* (2006.01)

(52) U.S. Cl.
CPC .............. *G01N 1/4077* (2013.01); *B01J 19/10* (2013.01); *C12Q 1/004* (2013.01); *G01N 1/08* (2013.01); *G01N 2001/4094* (2013.01)

(58) Field of Classification Search
CPC .................. G01N 1/4077; G01N 1/08; G01N 2001/4094; B01J 19/10; C12Q 1/004; B01L 3/502; B01L 2300/042; B01L 2300/0609; B01L 2300/0681; B01L 2300/0832
USPC .......................................................... 435/30
See application file for complete search history.

(56) References Cited

U.S. PATENT DOCUMENTS

| 8,158,379 B2 * | 4/2012 | Ronholdt | A61L 2/0011 435/31 |
|---|---|---|---|
| 8,669,070 B2 * | 3/2014 | Zajdowicz | C12Q 1/04 435/325 |
| 2014/0106394 A1 * | 4/2014 | Ko | B01L 3/50255 422/552 |

FOREIGN PATENT DOCUMENTS

| WO | WO-03019148 A1 * | 3/2003 | ............. B01L 3/502 |
|---|---|---|---|
| WO | WO-2018003104 A1 * | 1/2018 | ........... B01D 35/027 |

OTHER PUBLICATIONS

Get, Clear Plastic Pitcher with lid, Oct. 2012, p. 1, and 3 (Year: 2012).*

* cited by examiner

*Primary Examiner* — Gene O Crawford
*Assistant Examiner* — Muhammad Awais
(74) *Attorney, Agent, or Firm* — Kilpatrick Townsend & Stockton LLP; Jennifer Giordano-Coltart; Lana Kuchinski

(57) ABSTRACT

An extraction system for testing microbial contamination includes a biocompatible outer vessel that has a side wall and a biocompatible suspension system that is positionable within an interior of the biocompatible outer vessel. The biocompatible suspension system includes a horizontal member on which a sample may be supported and a securement mechanism that is engagable with the side wall of the biocompatible outer vessel to maintain the suspension system at a desired position within the biocompatible outer vessel.

20 Claims, 31 Drawing Sheets

EXTRACTION SYSTEM FOR TESTING MICROBIAL CONTAMINATION OF TISSUE PRODUCTS

CROSS-REFERENCES TO RELATED APPLICATIONS

This application claims the benefit of U.S. Provisional Application No. 62/656,254, filed Apr. 11, 2018, of which is assigned to the assignee hereof, and incorporated herein in its entirety by reference.

BACKGROUND

Certain medical procedures, such as reconstructive orthopedic procedures, can involve the use of tissue products, such as allografts (e.g., a tissue graft from a donor that is of the same species as the recipient, but not genetically identical), xenografts (e.g., a tissue graft from a donor that is of a different species than the recipient), and/or autografts (e.g., a tissue graft in which the donor and recipient are the same). During such medical procedures, various equipment, components, methods, or techniques can be used to detect microbial contamination of the tissue products before tissue transplantation.

For instance, a vessel containing an extraction fluid and a tissue product can be sonicated to release microorganisms from the tissue product into the extraction liquid and the extraction fluid containing the microorganisms can be tested to detect microbial contamination of the tissue product. However, such vessels may be unable to hold large or oddly shaped tissue products or do so in an efficient manner. Moreover, such vessels may not be suitable for testing microbial contamination of soft tissue types (e.g., skin) that may become folded or damaged during microbial contamination detection processes. Furthermore, conventional methods for microbial contamination detection may involve cotton swab or destructive testing methods or techniques. However, cotton swab testing methods may present several disadvantages such as, for example, the antibacterial effects of cotton, the inability of cotton swabs to maintain bacteria for extended periods of time, the inability of cotton swabs to be sensitive to microbial contamination detection from assorted surfaces (e.g., porous, freeze-dried, or frozen tissue products), or the inability of cotton swabs to interact with a full surface area of a tissue product (e.g., a cotton swab may miss crevices or specific folds that makeup a tissue product), which can lead to inaccurately detecting microbial contamination. Destructive testing methods may involve using a small quantity of an unfeasible or low-quality portion of a tissue product to detect microbial contamination of the entire tissue product. However, destructive testing methods also present several disadvantages including, for example, using a small quantity of a tissue product to detect microbial contamination of the entire tissue product, which can lead to inaccurately detecting microbial contamination of the entire tissue product, and use of valuable tissue only for testing.

Thus, existing systems and methods for detecting microbial contamination of a tissue product present disadvantages such as, but not limited to, those discussed above. As a result, existing systems and methods may inaccurately detect microbial contamination of a tissue product, which can expose a recipient of the tissue product to a risk of infection.

SUMMARY

Embodiments of the present disclosure are directed to extraction systems and method for testing microbial contamination of tissue products. These systems and methods provide biocompatible solutions that enable tissue products to be submerged in an extraction fluid that may be agitated to detect any microbial contaminants present on the tissue product prior to transplantation and/or other medical usage of the tissue product.

In one embodiment, an extraction system for testing microbial contamination is provided. The extraction system may include a biocompatible outer vessel having a side wall and a biocompatible suspension system that is positionable within an interior of the biocompatible outer vessel. The biocompatible suspension system may include a horizontal member on which a tissue sample may be supported and a securement mechanism that is engagable with the side wall of the biocompatible outer vessel to maintain the suspension system at a desired position within the biocompatible outer vessel.

In some embodiments, the securement mechanism may include at least one hook that is configured to engage a top end of the side wall. The biocompatible suspension system may include at least one vertical member that is coupled with the horizontal member and the securement mechanism. The biocompatible suspension system may include a clamp that is coupled with the horizontal member. The clamp may be configured to secure a sample to the biocompatible suspension system. In some embodiments, the clamp may be movable along a length of the horizontal member. In some embodiments, the biocompatible outer vessel may have a thickness of between about 0.5 and 3 millimeters. The biocompatible outer vessel may include at least one of a spout, a flange, or a handle.

In another embodiment, an extraction system for testing microbial contamination includes a biocompatible outer vessel and one or both of a biocompatible inner vessel or a biocompatible suspension system. The biocompatible inner vessel may be positionable within the biocompatible outer vessel. The biocompatible inner vessel may have a height of approximately thirteen inches and a diameter of approximately four inches. The biocompatible inner vessel may include a handle coupled to the biocompatible inner vessel. The biocompatible suspension system may be positionable within the biocompatible outer vessel. Soft tissue may be positionable on the biocompatible suspension system. The extraction system may be configured to receive a tissue product having a size of at least thirty centimeters.

In some embodiments, the biocompatible suspension system may include a curved portion that is configured to secure the biocompatible suspension system to a top end of the biocompatible outer vessel. In some embodiments, the biocompatible suspension system may include a first vertical member, a second vertical member, and a horizontal member that extends between and couples with the first vertical member and the second vertical member. The horizontal member may be configured to support the tissue sample. The biocompatible outer vessel may have a height of between about 4 inches and thirty inches, and in some embodiments may have a diameter of between approximately 2 inches and 8 inches. The biocompatible outer vessel may include at least one of a spout, a flange, or a handle. In some embodiments, the biocompatible outer vessel may include a perforated sheet.

In another embodiment, a method of using an extraction system is provided. The method may include securing the tissue sample to a horizontal member of a biocompatible suspension system and submerging at least a portion of the tissue sample in an extraction fluid provided within an interior of a biocompatible outer vessel. The method may also include agitating the extraction fluid for a predetermined period of time to release microorganism from the tissue sample and removing the extraction fluid from the biocompatible outer vessel. The method may further include analyzing the extraction fluid for microbial contamination.

In some embodiments, the method may also include removing the biocompatible suspension member and the tissue sample from the biocompatible outer vessel prior to removing the extraction fluid. In some embodiments, the extraction fluid may be agitated using a sonicator. In one embodiment, securing the tissue sample to the horizontal member may involve clamping the tissue sample to the horizontal member using at least one clamp. In some embodiments, the extraction fluid may be removed from the biocompatible outer vessel while the extraction fluid is being agitated, while in other embodiments the extraction fluid may be removed after agitation of the extraction fluid has been completed. In one embodiment, submerging the at least a portion of the tissue sample in the extraction fluid may include coupling a securement mechanism of the biocompatible suspension system to a top end of the biocompatible outer vessel.

DETAILED DESCRIPTION

Figure 1:
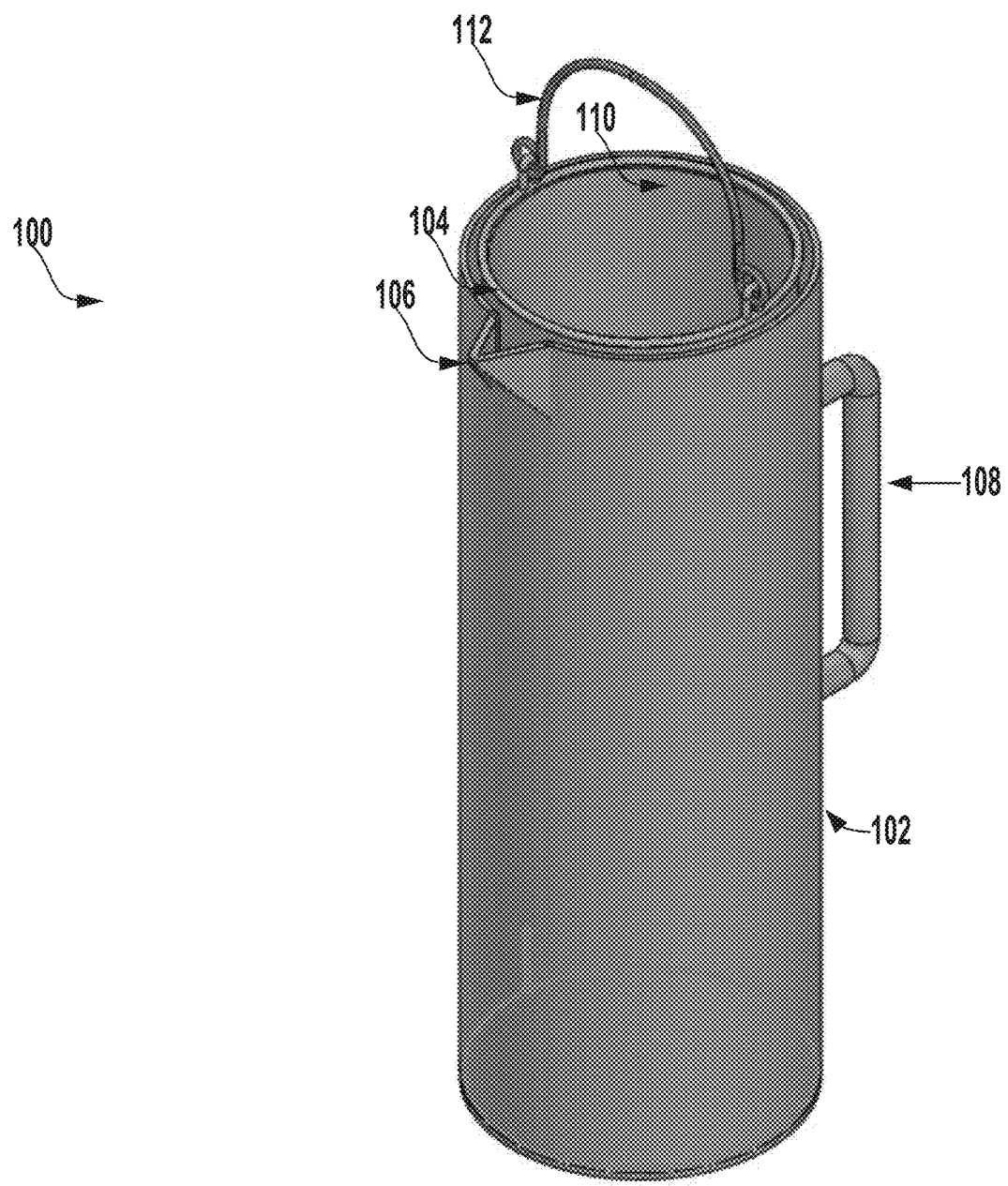
FIG. 1 is a perspective view of an extraction system for testing microbial contamination of tissue products, according to one example of the present disclosure.

Certain aspects and features of the present disclosure are directed to an extraction system for testing microbial contamination of tissue products. The extraction system can include an outer vessel (e.g., chamber) and an inner vessel positioned within the outer vessel. In some instances, the inner and outer vessels can each be made of a biocompatible stainless steel material. In some instances, the inner and outer vessels can each have a circular cross-section (e.g., the inner and outer vessels can each have a cylindrical shape), though other cross-sectional shapes are contemplated.

In some instances, the outer vessel can have a first end (e.g., a top end) and a second end (e.g., a bottom end). The first end of the outer vessel can include a spout (e.g., a portion of the first end that extends away from the first end). In some examples, the outer vessel can also include a handle, a flange, or a lid, each of which can be coupled (e.g., attached or connected) to the outer vessel. In some instances, the flange may be coupled to the second end of the outer vessel and can extend away from the second end (e.g., extend approximately one inch away from a circumference of the second end), which can allow the flange to stabilize the extraction system during sonication operations and reduce vibration during such sonication operations. In another example, the flange may extend between approximately 0.5 inches and approximately three inches away from a circumference of the second end of the outer vessel. In some embodiments, the outer vessel can have a height (e.g., length) of approximately fourteen inches. In another example, the outer vessel can have a height between approximately four inches and approximately thirty inches. In still another example, the outer vessel can have a height that is greater than thirty centimeters. As an example, the outer vessel can have a height of thirty-three centimeters. In some examples, the outer vessel can have an inner diameter of approximately four inches. As an example, the outer vessel can have an inner diameter of approximately 4.60 inches. In still another example, the outer vessel can have an inner diameter between approximately twelve centimeters and approximately eleven centimeters. As an example, the outer vessel can have an inner diameter between approximately 11.351 centimeters and approximately 11.509 centimeters. In some examples, the outer vessel can have an average diameter between approximately two inches and approximately eight inches. In some examples, the outer vessel can have a thickness between approximately 0.5 millimeters and approximately three millimeters. In some instances, the outer vessel can have any size or thickness that facilitates or allows transmission of sonic or sound energy from a sonicator device.

In some examples, the inner vessel of the extraction system can be a stainless-steel perforated sheet. Generally, the inner vessel may have a height that is the same as or 0.5%, 1%, 2%, 3%, 4%, 5%, 10%, 15%, or 20% shorter than the height of the outer vessel. In some instances, the inner vessel may have a height that is longer than the height of the outer vessel by 0.5%, 1%, 2%, 3%, 4%, 5%, 7%, 10%, or 15%. In such instances, the upper end of inner vessel may extend above the upper end of the outer vessel. In one example, the inner vessel can have a height of approximately thirteen inches and a diameter of approximately four inches (e.g., 4.2 inches). In some examples, a height, size, or thickness of the inner vessel can be proportional to a height, size, or thickness of the outer vessel. In some instances, a handle can be coupled to an end (e.g., a top end) of the inner vessel.

In this manner, the extraction system can be configured such that one or more tissue products can be positioned within the inner vessel, and the inner vessel, along with an extraction fluid, can be positioned within the outer vessel. The tissue product and extraction fluid can be positioned within the outer vessel such that the tissue product is submerged within the extraction fluid. As an example, the inner vessel may be a stainless-steel perforated sheet that can allow the extraction fluid to flow into the inner vessel to submerge the tissue product. In some instances, the extraction fluid, along with the tissue product, can be agitated (e.g., sonicated) for a period of time to release microorganisms from the tissue product and into the extraction fluid. Subsequently, the inner vessel containing the tissue product can be removed from within the outer vessel, and the extraction fluid that contains released microorganisms can be removed from the outer vessel (e.g., via the spout of the outer vessel and using the handle of the outer vessel) and analyzed for microbial contamination (e.g., cultured to determine if microbial contamination is present).

In some embodiments, the extraction system can include a suspension system instead of the inner vessel, and the suspension system can be inserted or positioned within the outer vessel of the extraction system. In some examples, the extraction system can include the suspension system such that soft tissue (e.g., skin, fascia, placental tissues, tendons, etc.) can be placed on, or clamped onto (e.g., via one or more fixed or movable clamps), one or more components of the suspension system, which can allow the extraction system to be sonicated to detect microbial contamination of the soft tissue in substantially the same manner as described above. In some examples, the suspension system can include one or more components that can be made of any suitable material for testing microbial contamination of tissue products. For instance, the suspension system can include one or more rods that can be made of a biocompatible stainless steel material. As an example, the suspension system can include various biocompatible stainless steel horizontal rods coupled or connected to various biocompatible stainless steel vertical rods. The suspension system may include one, two, three, four, or five vertical rods. In some instances, the suspension system may include up to six vertical rods. The suspension system may include one, two, three, four, or five horizontal rods. In some instances, the suspension system may include up to six horizontal rods. The horizontal or vertical rods can be of any suitable size or length. Generally, the vertical rods may have a height that is the same as or 0.5%, 1%, 2%, 3%, 4%, 5%, 10%, 15%, or 20% shorter than the height of the outer vessel. In some instances, the vertical rods may have a height that is longer than the height of the outer vessel by 0.5%, 1%, 2%, 3%, 4%, 5%, 7%, 10%, or 15%.] In such instances, the upper end of vertical rods may extend above the upper end of the outer vessel. For example, the vertical rods can each have a length of approximately thirteen inches. The horizontal rods can be coupled to the vertical rods and spaced or positioned along a length of the vertical rods such that the horizontal rods are positioned along a length of the inner vessel within which the suspension system is positioned.

As an example, the suspension system can include two vertical rods and a first horizontal rod can be positioned between the two vertical rods and coupled to the two vertical rods. The first horizontal rod can be coupled to the vertical rods at a position that is approximately at a center of the inner vessel. A second horizontal rod can be positioned between the vertical rods and coupled to the vertical rods at a position that is above the first horizontal rod and proximate to the first end (e.g., top end) of the inner vessel. A third horizontal rod can be positioned between the vertical rods and coupled to the vertical rods at a position that is below the first horizontal rod and proximate to a second end (e.g., bottom end) of the inner vessel.

In some instances, a first end (e.g., a top end) of the suspension system can include one or more hooks or other components that can be configured for coupling the suspension system to the extraction system. In some instances, the suspension system can include hooks configured for coupling the suspension system to a first end (e.g., top end) of the outer vessel of the extraction system. In some instances, the suspension system can include hooks, clamps, or other fasteners configured for coupling soft tissue to the suspension system.

In some instances, the suspension system is configured to be inserted or positioned within an inner vessel as described herein that is positionable within the outer vessel of the extraction system. In such instances, the vertical rods may have a height that is the same as or 0.5%, 1%, 2%, 3%, 4%, 5%, 10%, 15%, or 20% shorter than the height of the inner vessel. In some instances, the vertical rods may have a height that is longer than the height of the inner vessel by 0.5%, 1%, 2%, 3%, 4%, 5%, 7%, 10%, or 15%. Other aspects of the relationship between the suspension system and the outer vessel as described herein are also applicable to configurations where the suspension system is positionable within the inner vessel of the extraction system.

Embodiments of the present disclosure provide advantages over previous solutions for detecting microbial contamination of a tissue product. For example, systems and methods described herein provide the ability to detect microbial contamination of a wide variety of tissue products (e.g., large or oddly shaped tissue products). Moreover, systems and methods described herein provide the ability to detect microbial contamination of soft tissue types and mitigate the risk of damaging or folding such soft tissues during microbial contamination detection processes. Furthermore, systems and methods described herein can obviate the use of cotton swab or destructive testing methods or techniques, which can inaccurately detecting microbial contamination and expose a recipient of a tissue product to a risk of infection. In addition, systems and methods described herein can minimize a volume of extraction fluid produced during microbial contamination detection operations, which can improve accuracy in testing and may also be more cost effective.

The following illustrative examples are given to introduce the general subject matter discussed here and are not intended to limit the scope of the disclosed concepts. The following sections describe various additional features and examples with reference to the drawings in which like numerals indicate like elements, and directional descriptions are used to describe the illustrative examples but, like the illustrative examples, should not be used to limit the present disclosure.

FIG. 1 is a perspective view of an extraction system 100 for testing microbial contamination of tissue products, according to one example of the present disclosure.

In this example, the extraction system 100 includes an outer vessel 102 and an inner vessel 104 positioned within the outer vessel 102. The outer vessel 102 and the inner vessel 104 can each have a circular cross-section and can have a cylindrical shape. In other examples, the outer vessel 102 or the inner vessel 104 can have any suitable cross-section or shape such as, for example, square, triangular, oval, trapezoidal, rectangular, or other cross-sections. In some examples, the outer vessel 102 and the inner vessel 104 can have the same shape or cross-section. In another example, the outer vessel 102 and the inner vessel 104 can have different shapes or cross-sections.

The inner vessel 104 can include an opening 110 at a first end (e.g., a top end) of the inner vessel 104, which can allow a tissue product (e.g., a head of a femur or femoral shafts) to be positioned within the inner vessel 104. In some examples, the inner vessel 104 can include a handle 112 that is coupled to the inner vessel 104.

In some examples, the extraction system 100 can be configured such that a tissue product having a size (e.g., length) of at least thirty centimeters can be positioned within the extraction system 100 (e.g., within the inner vessel 104). In some examples, a size of the extraction system 100 can be less than approximately 29.2×24.1 cm$^2$. In some examples, a size of the extraction system 100 can be less than approximately 704.83 cm$^2$. In some examples, the one or more components of the extraction system 100 can have a combined thickness that is less than approximately 0.635 cm. In another example, the outer vessel 102 can have a thickness that is less than approximately 0.635 cm. In some examples, the extraction system 100 or a component of the extraction system 100 can have any suitable size or thickness for testing microbial contamination of tissue products. In some examples, one or more components of the extraction system 100 can have a size or thickness that is suitable for sonication operations for testing microbial contamination of allograft tissue or other tissue products (e.g., a size or thickness that facilitates or allows transmission of sonic or sound energy from a sonicator device).

In some examples, one or more components of the extraction system 100 can be made of any material that is capable of withstanding temperatures above approximately one hundred and thirty degrees Celsius (e.g., any material having a melting point greater than approximately one hundred and thirty degrees Celsius). In some examples, one or more components of the extraction system 100 can be made of any material that is capable of enduring (e.g., withstanding) sonication at a frequency of at least approximately 40 kHz. In some examples, one or more components of the extraction system 100 can be made of any material that is capable of enduring sonication at a frequency of at least approximately 32 kHz. In some examples, one or more components of the extraction system 100 can be made of any material that is capable of enduring sonication at a frequency of at least approximately 40 kHz. As an example, one or more components of the extraction system 100 can be made of any material that is capable of enduring sonication at a frequency between approximately 36 kHz and 48 kHz. As another example, one or more components of the extraction system 100 can be made of any material that is capable of enduring sonication at a frequency between approximately 34 kHz and 46 kHz.

In some examples, one or more components of the extraction system 100 can be made of any material that is capable of enduring sonication at an intensity of at least approximately 50 Watts per gallon. In some examples, one or more components of the extraction system 100 can be made of any material that is capable of enduring sonication at an intensity between approximately 50 Watts per gallon and approximately 200 Watts per gallon. In some examples, one or more components of the extraction system 100 can be made of any material that is capable of enduring sonication at an intensity between approximately 100 Watts per gallon and approximately 550 Watts per gallon. In some examples, one or more components of the extraction system 100 can be made of any material that is capable of enduring sonication at an intensity between approximately 200 Watts per gallon and approximately 400 Watts per gallon.

In some examples, the extraction system 100 or a component of the extraction system 100 can be made of any suitable material for testing microbial contamination of tissue products. The various components of the extraction system 100 can be fabricated using any suitable method or technique including, for example, three-dimensional printing methods and techniques.

Figure 2:
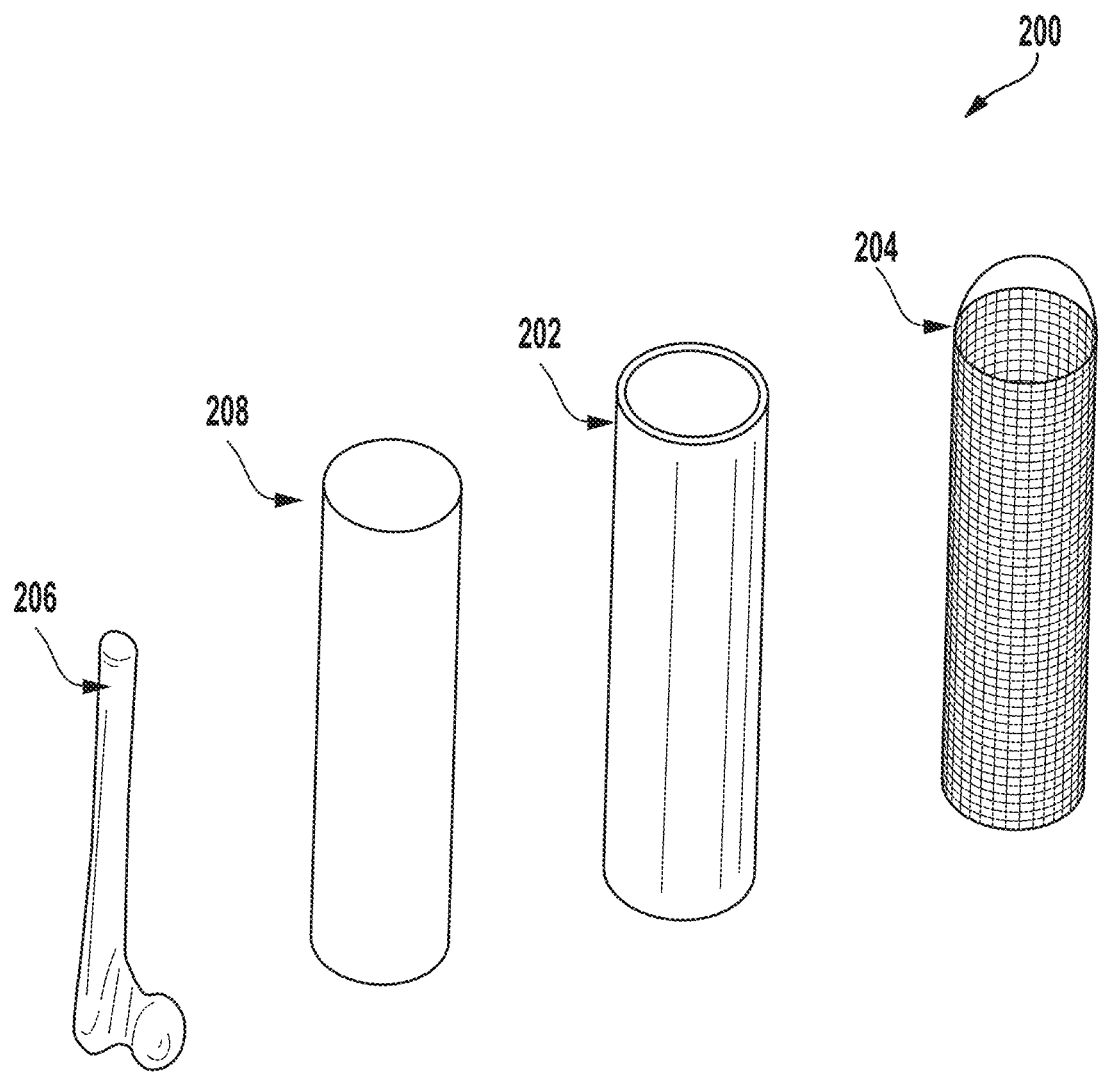
FIG. 2 is an exploded perspective view of components of an extraction system for testing microbial contamination of tissue products, according to one example of the present disclosure.

FIG. 2 is an exploded perspective view of components of an extraction system 200 for testing microbial contamination of tissue products, according to one example of the present disclosure. In the example depicted in FIG. 2, the extraction system 100 includes the outer vessel 202 and the inner vessel 204.

In some examples, the extraction system 200 can be configured such that one or more tissue products 206 such as, for example, a head of a femur, can be positioned within the inner vessel 204. The tissue product 206, along with the inner vessel 204, can be positioned within the outer vessel 202 and an extraction fluid 208 (e.g., water or other suitable fluid) can be dispersed into the outer vessel 202. The tissue product 206 and the inner vessel 204 can be positioned within the outer vessel 202 such that the tissue product 206 is submerged within the extraction fluid 208. As an example, the inner vessel 204 may be a stainless steel perforated sheet that allows the extraction fluid 208 to flow into the inner vessel 204 to submerge the tissue product 206.

Figure 3:
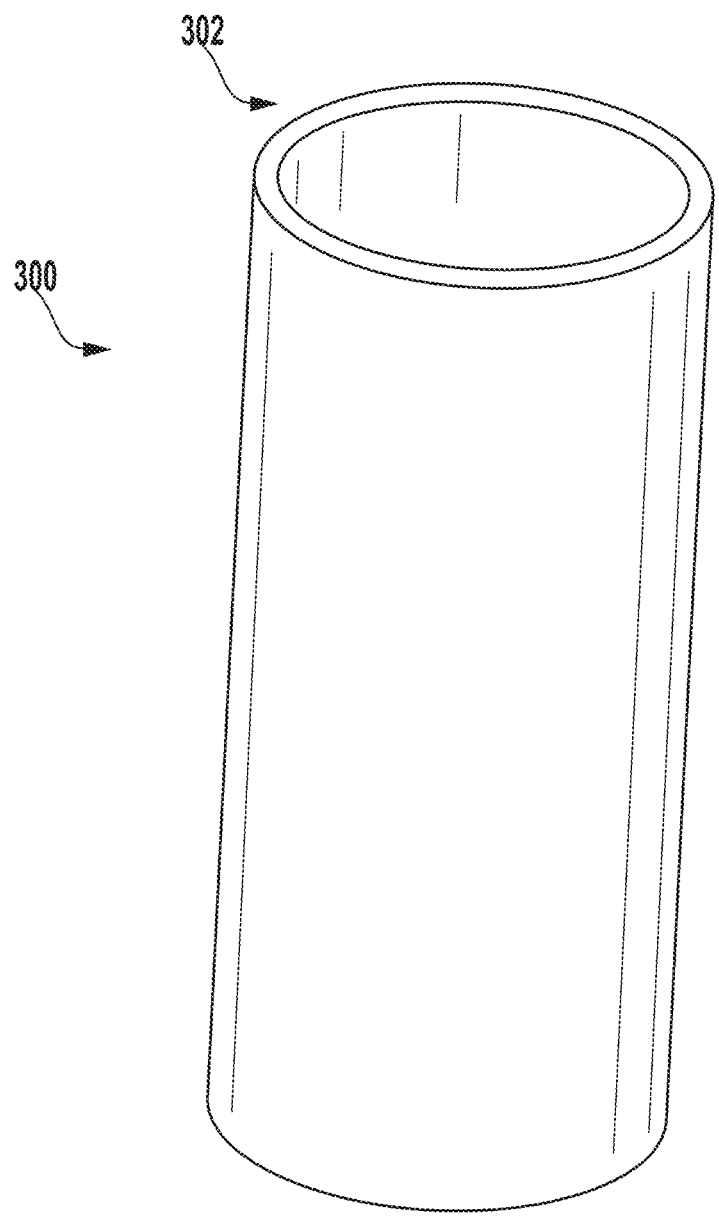
FIG. 3 a perspective view of an outer vessel of an extraction system for testing microbial contamination of tissue products, according to one example of the present disclosure.

FIG. 3 a perspective view of an outer vessel 300 of an extraction system (e.g., the outer vessel 202 of the extraction system 200 of FIG. 2) for testing microbial contamination of tissue products, according to one example of the present disclosure.

In some embodiments, the outer vessel 300 can be made of any of biocompatible stainless steel (e.g., 316 or 304 stainless steel), a biocompatible polycarbonate material, glass, titanium, etc. In some examples, the outer vessel 300 can be made of any material that is capable of withstanding temperatures above approximately one hundred and thirty degrees Celsius (e.g., any material having a melting point greater than approximately one hundred and thirty degrees Celsius). In another example, the outer vessel 300 can be made of any suitable material for testing microbial contamination of tissue products.

The outer vessel 300 can have a height (e.g., length) of approximately fourteen inches. In another example, the outer vessel 300 can have a height between approximately four inches and approximately thirty inches. In still another example, the outer vessel 300 can have a height that is greater than thirty centimeters. As an example, the outer vessel 300 can have a height of thirty-three centimeters.

In some examples, the outer vessel 300 can have an outer diameter of approximately five inches. In another example, the outer vessel 300 can have an outer diameter between approximately twelve centimeters and thirteen centimeters. As an example, the outer vessel 300 can have an outer diameter between approximately 12.621 centimeters and 12.779 centimeters. In some examples, the outer vessel 300 can have an inner diameter of approximately four inches. As an example, the outer vessel 300 can have an inner diameter of approximately 4.60 inches. In still another example, the outer vessel 300 can have an inner diameter between approximately twelve centimeters and approximately eleven centimeters. As an example, the outer vessel 300 can have an inner diameter between approximately 11.351 centimeters and approximately 11.509 centimeters. In some examples, the outer vessel 300 can have an average diameter between approximately two inches and approximately eight inches.

In some examples, the outer vessel 300 can have any suitable height, diameter, shape, or configuration for testing microbial contamination of tissue products.

In some instances, the outer vessel 300 can have a first end (e.g., a top end) and a second end (e.g., a bottom end). In some examples, the first end of the outer vessel 300 can include a spout (e.g., a projecting portion of the first end that extends away from the first end). For example, and with reference to FIG. 1, the outer vessel 300 can include a spout 106 at a first end of the outer vessel 300.

In some examples, the outer vessel 300 can also include a handle, a flange, or a lid, each of which can be coupled or connected to the outer vessel 300. For example, and with reference to FIG. 1, the outer vessel 300 can include a handle 108.

Returning to FIG. 3, in some examples, the outer vessel 300 can include an opening 302 at a first end (e.g., a top end) of the outer vessel 300, which can allow an inner vessel of an extraction system 100 (e.g., the inner vessel 204 of FIG. 2 or any other inner vessel or suspension system described herein) to be positioned within the outer vessel 300.

In some instances, outer vessel 300 can include a flange that may be coupled (e.g., attached or connected) to a second end (e.g., bottom end) of the outer vessel 300 and the flange can extend away from the second end (e.g., extend approximately one inch away from a circumference of the second end), which can allow the flange to stabilize the outer vessel 300 or an extraction system (e.g., the extraction system of FIGS. 1-2) during sonication operations and reduce vibration during such sonication operations.

Figure 4:
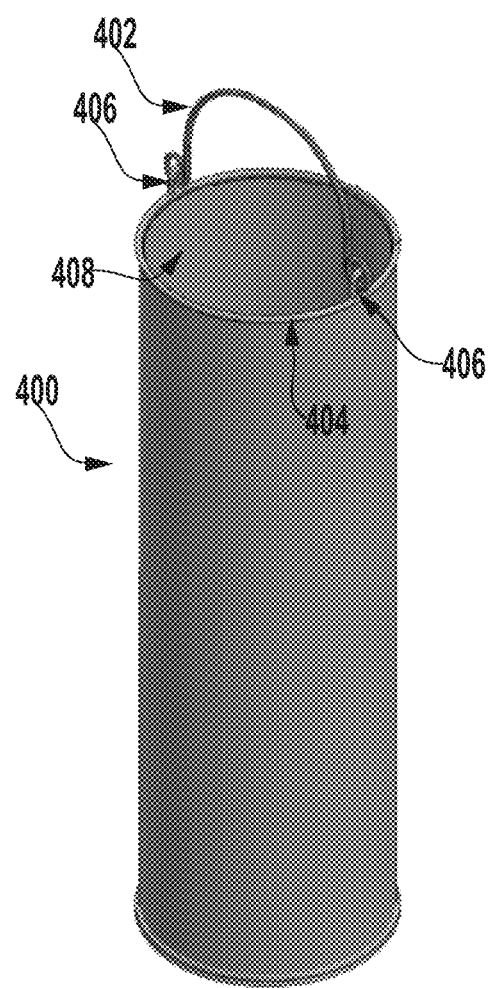
FIG. 4 a perspective view of an inner vessel of an extraction system for testing microbial contamination of tissue products, according to one example of the present disclosure.

FIG. 4 a perspective view of an inner vessel 400 of an extraction system for testing microbial contamination of tissue products, according to one example of the present disclosure.

In some embodiments, the inner vessel 400 can be made of any of biocompatible stainless steel (e.g., 316 or 304 stainless steel), a biocompatible polycarbonate material, glass, titanium, etc. In some examples, the inner vessel 400 can be a stainless steel perforated sheet. As an example, the inner vessel 400 can be a 316 stainless steel wire cloth or a 316 stainless steel perforated sheet that includes openings, which can be of various sizes such as, for example, approximately 0.69 cm or approximately 0.63 cm openings. In other examples, the inner vessel 400 can include openings of any suitable size, shape, or configuration. In some examples, the inner vessel 400 can be any size, shape, or configuration suitable for retaining an allograft or other tissue product within the inner vessel 400 and allowing an extraction fluid to flow through the inner vessel 400 and around the allograft or other tissue product positioned within the inner vessel 400.

In some examples, the inner vessel 400 can be made of any material that is capable of withstanding temperatures above approximately one hundred and thirty degrees Celsius (e.g., any material having a melting point greater than approximately one hundred and thirty degrees Celsius). In another example, the inner vessel 400 can be made of any suitable material for testing microbial contamination of tissue products.

In one example, the inner vessel 400 can have a height of approximately thirteen inches and a diameter of approximately four inches. As an example, the inner vessel 400 can have a diameter of approximately 4.2 inches. In some examples, the inner vessel 400 can have any suitable thickness including, for example, a thickness of approximately 0.15 centimeters. In another example, the inner vessel 400 can have a thickness between approximately 0.05 centimeters and approximately 0.3 centimeters.

In some examples, the inner vessel 400 can have any suitable height, diameter, or shape for testing microbial contamination of tissue products and for being positionable within an outer vessel of an extraction system.

In some examples, the inner vessel 400 can include a handle 402 that is coupled to a portion of the inner vessel 400. In some instances, the handle 402 can be made of the same material as the inner vessel 400 (e.g., 316 or 304 stainless steel, biocompatible polycarbonate material, etc.) or any suitable material for testing microbial contamination of tissue products. In this example, the handle 402 can be coupled to a ring support 404 of the inner vessel 400 that is coupled to a first end (e.g., a top end) of the inner vessel 400. The handle 402 can be coupled to the ring support 404 via one or more side supports 406 coupled to the ring support 404.

Figure 5:
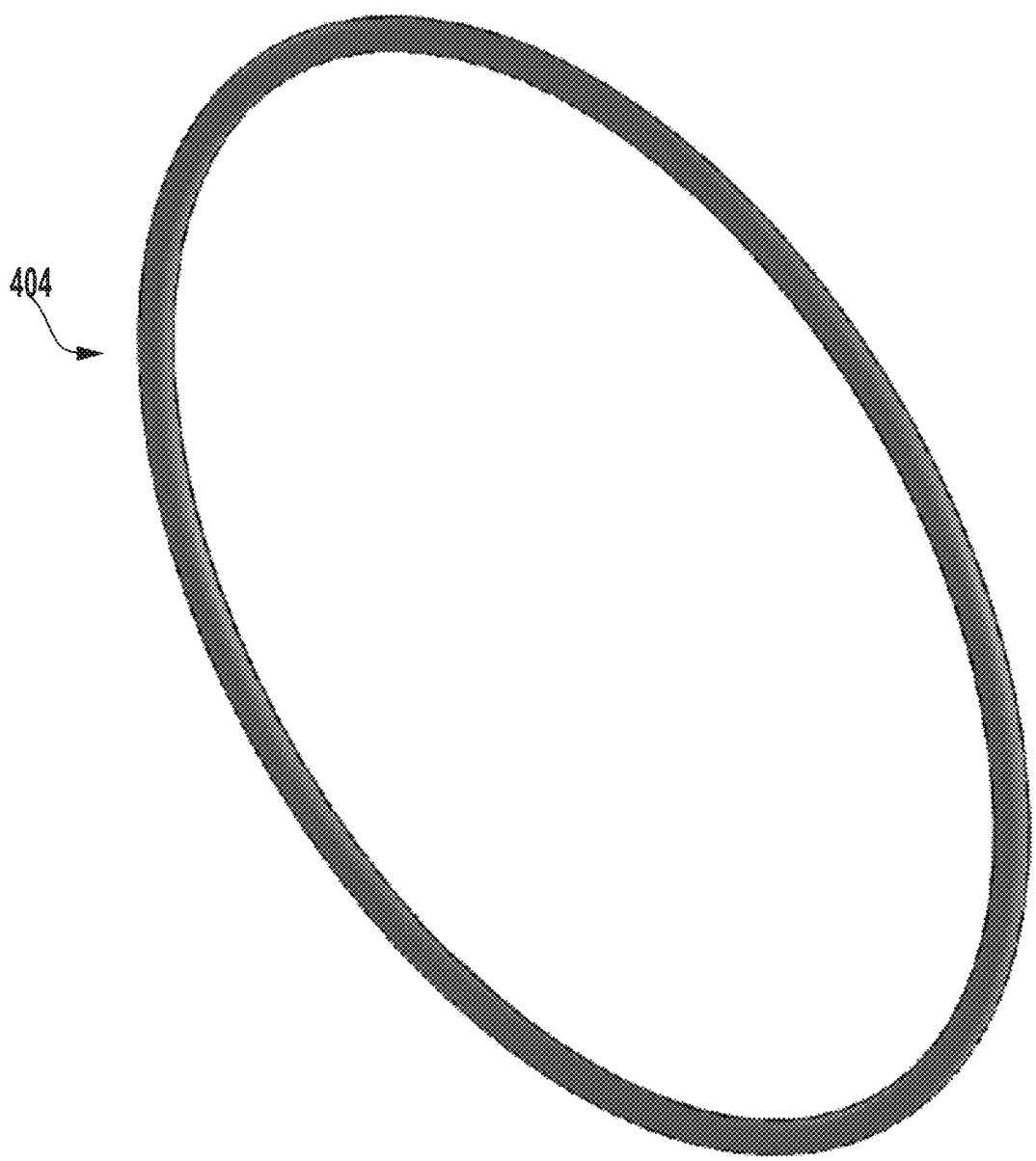
FIG. 5 a perspective view of a ring support of an inner vessel of an extraction system for testing microbial contamination of tissue products, according to one example of the present disclosure.

For example, FIG. 5 a perspective view of a ring support 404 of an inner vessel (e.g., the inner vessel 400 of FIG. 4) of an extraction system for testing microbial contamination of tissue products, according to one example of the present disclosure. In some examples, the ring support 404 can be configured for coupling a handle (e.g., the handle 402 of FIG. 4) to the inner vessel.

Figure 6:
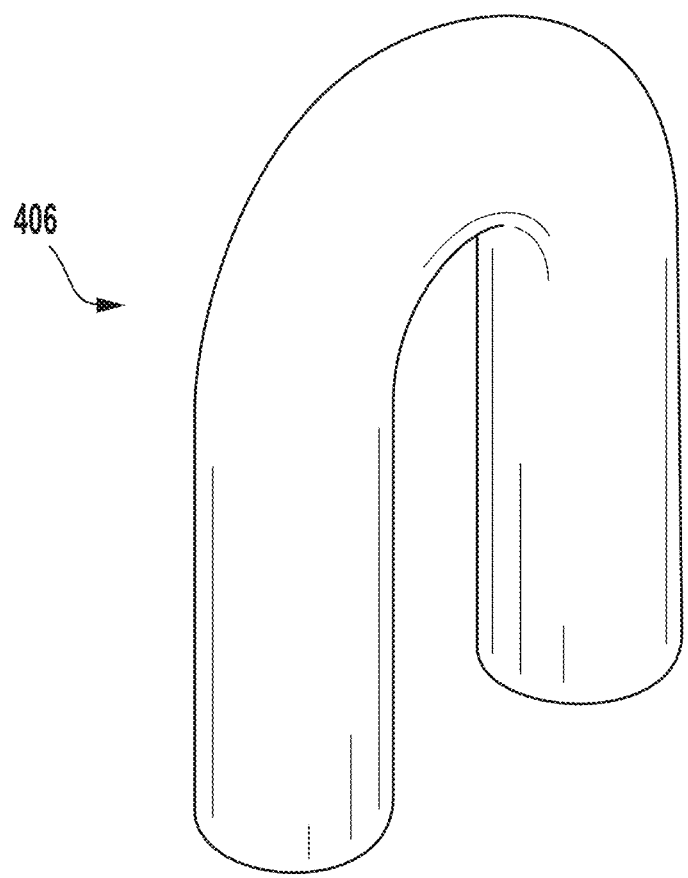
FIG. 6 a perspective view of a side support of an inner vessel of an extraction system for testing microbial contamination of tissue products, according to one example of the present disclosure.

FIG. 6 a perspective view of a side support 406 of an inner vessel (e.g., the inner vessel 400 of FIG. 4) of an extraction system for testing microbial contamination of tissue products, according to one example of the present disclosure. In some examples, the side support 406 can be configured for coupling a handle (e.g., the handle 402 of FIG. 4) to a ring support (e.g., the ring support 404 of FIGS. 4-5) of an inner vessel.

Figure 7:
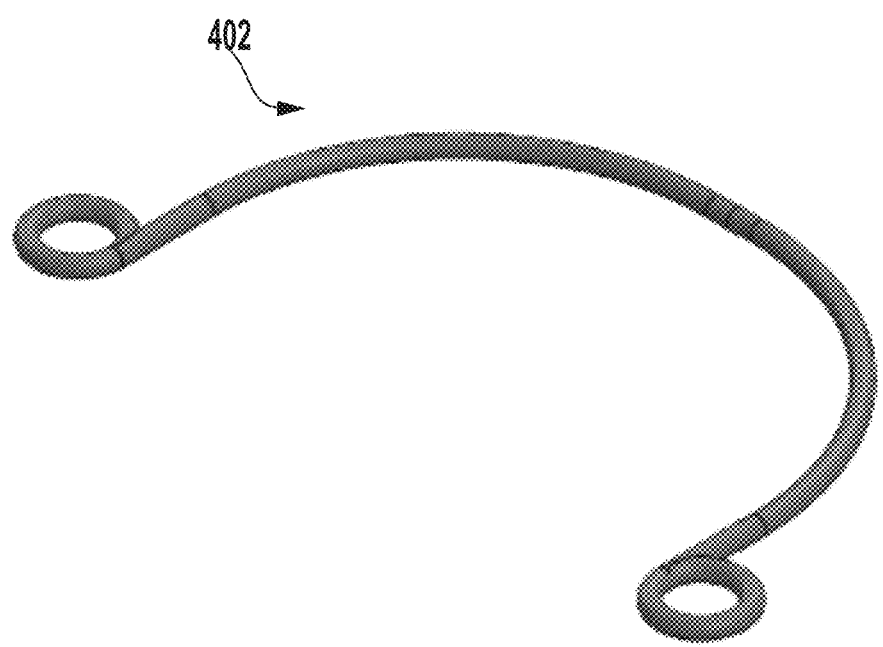
FIG. 7 a perspective view of a handle of an inner vessel of an extraction system for testing microbial contamination of tissue products, according to one example of the present disclosure.

FIG. 7 a perspective view of a handle 402 of an inner vessel (e.g., the inner vessel 400 of FIG. 4) of an extraction system for testing microbial contamination of tissue products, according to one example of the present disclosure. Other handle configurations are also contemplated.

Figure 8:
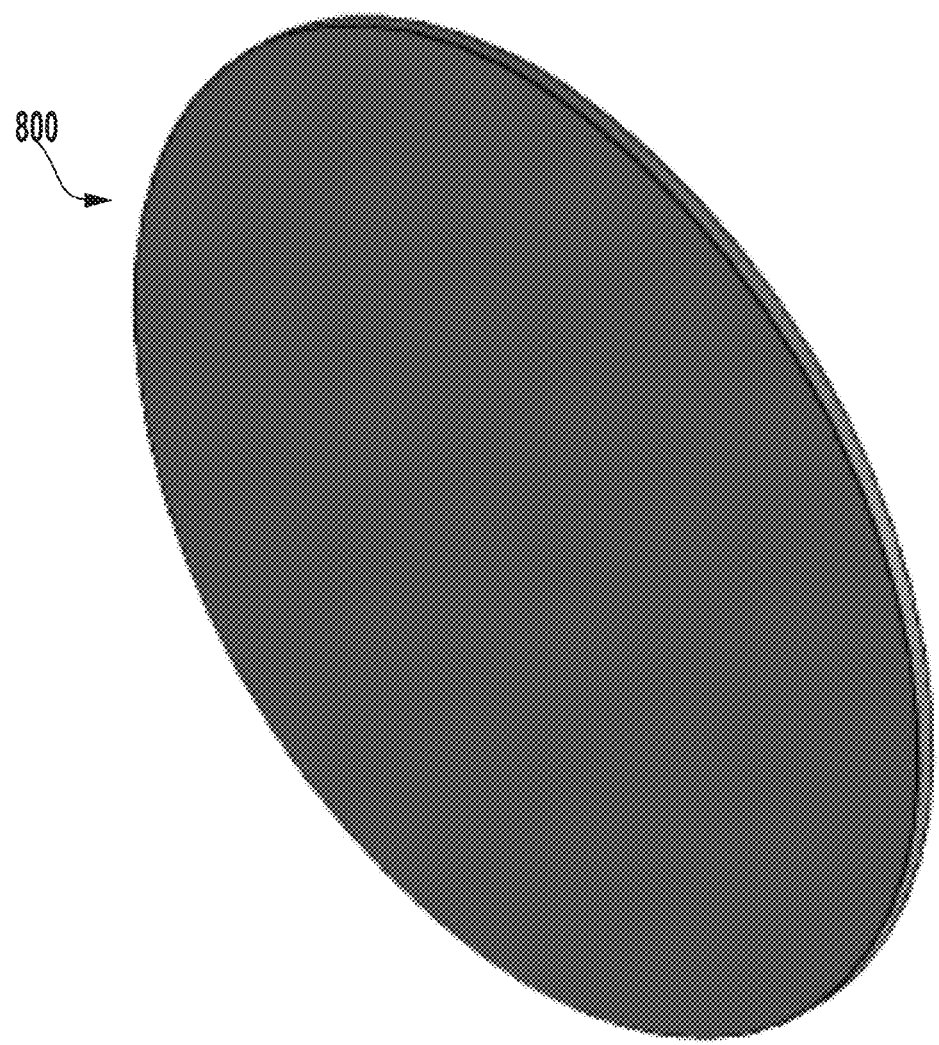
FIG. 8 a perspective view of a cap of an inner vessel of an extraction system for testing microbial contamination of tissue products, according to one example of the present disclosure.

Returning to FIG. 4, in some examples, the inner vessel 400 can include a cap or lid, which can be coupled to the first end of the inner vessel 400 to seal the inner vessel 400. For example, FIG. 8 a perspective view of a cap 800 of an inner vessel (e.g., the inner vessel 400 of FIG. 4) of an extraction system for testing microbial contamination of tissue products, according to one example of the present disclosure.

Also in reference to FIG. 4, the inner vessel 400 can also include an opening 408 at the first end (e.g., the top end) of the inner vessel 400, which can allow a tissue product (e.g., the tissue product 206 of FIG. 2) to be positioned within the inner vessel 400.

Figure 9:
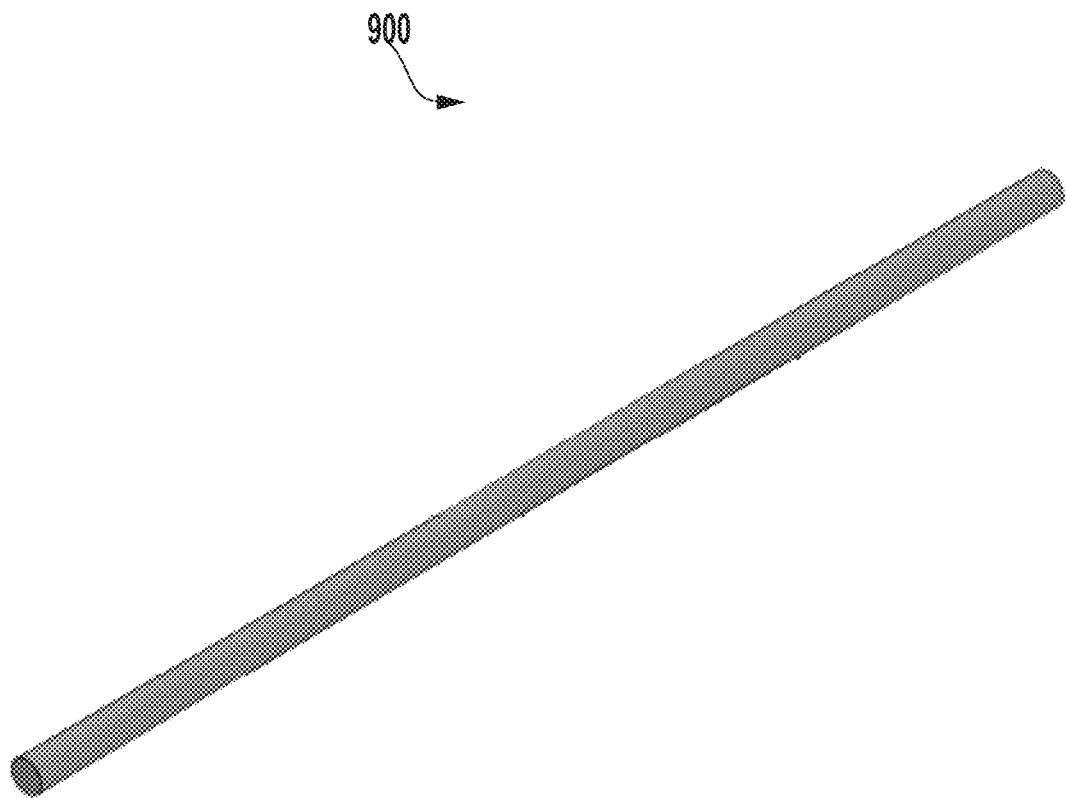
FIG. 9 a perspective view of a bottom support of an inner vessel of an extraction system for testing microbial contamination of tissue products, according to one example of the present disclosure.

FIG. 9 a perspective view of a bottom support 900 of an inner vessel of an extraction system for testing microbial contamination of tissue products, according to one example of the present disclosure. In some examples, the bottom support 900 can be of any shape, size, or thickness such that the bottom support 900 can support one or more components of the inner vessel. As an example, the bottom support 900 can provide rigidity to the inner vessel (e.g., to maintain an integrity of a shape of the inner vessel), which can prevent the inner vessel from bowing or bulging. For instance, the bottom support 900 can be a rod, a ring, etc. for providing rigidity to the inner vessel. In some examples, the inner vessel can include one or more bottom supports 900 that are positioned vertically, horizontally, or in a weave pattern on or within the inner vessel. In some instances, the one or more bottom supports can be positioned at any suitable location on the inner vessel including, for example, proximate to a first end (e.g., a top end) of the inner vessel, proximate to a center of the inner vessel, or proximate to a second end (e.g., a bottom end) of the inner vessel. In some instances, one or more vertical support rods may be positioned vertically along the inner or outer walls that form the sides of the inner vessel. In some instances, one or more ring-shaped support rods may be positioned along the inner or outer walls of the inner vessel. Such ring-shaped rods may be affixed to one or more vertical support rods.

Figure 10:
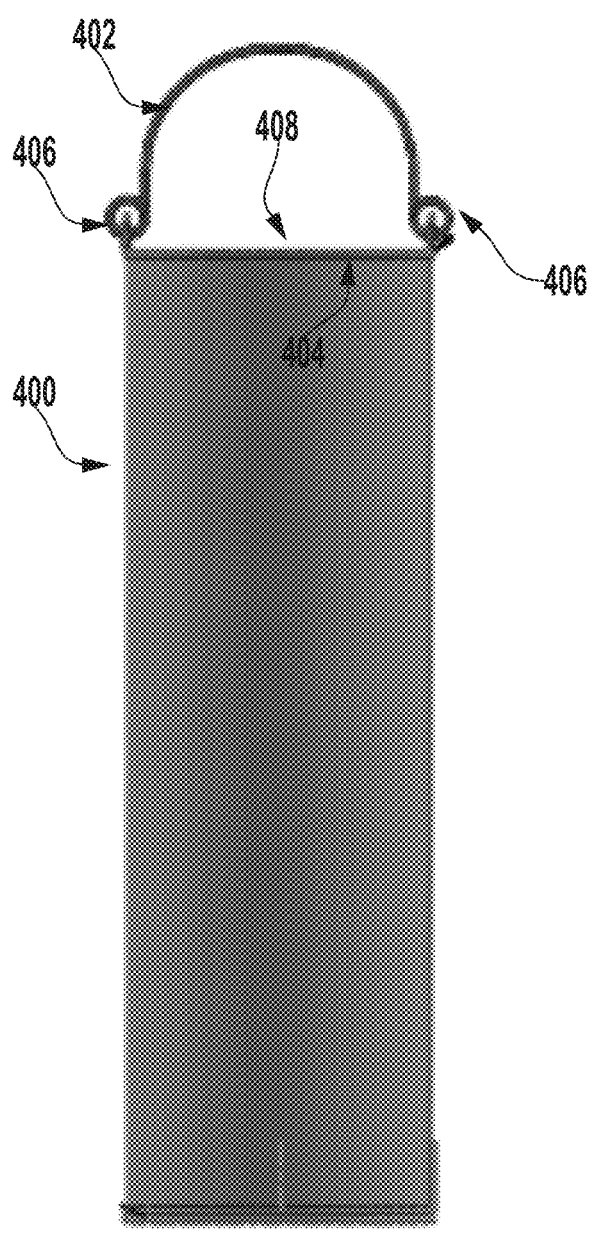
FIG. 10 a front view of the inner vessel of FIG. 4.

FIG. 10 a front view of the inner vessel of FIG. 4.

Figure 11:
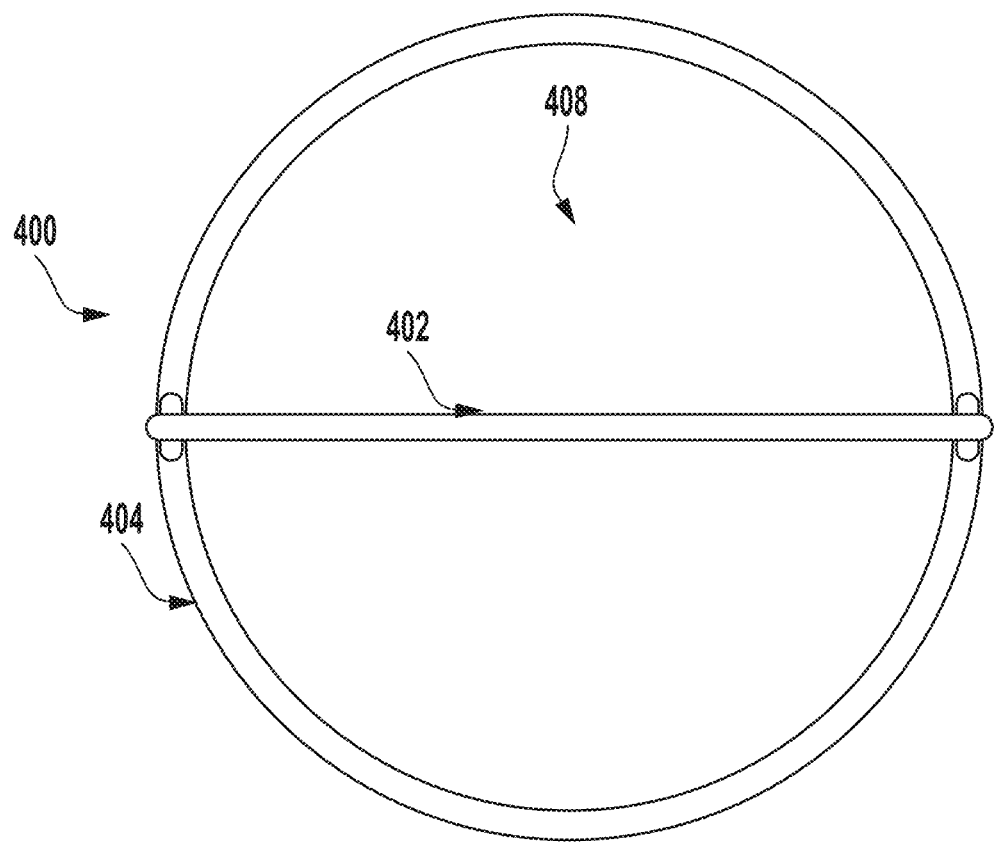
FIG. 11 a top view of the inner vessel of FIG. 4.

FIG. 11 a top view of the inner vessel of FIG. 4.

Figure 12:
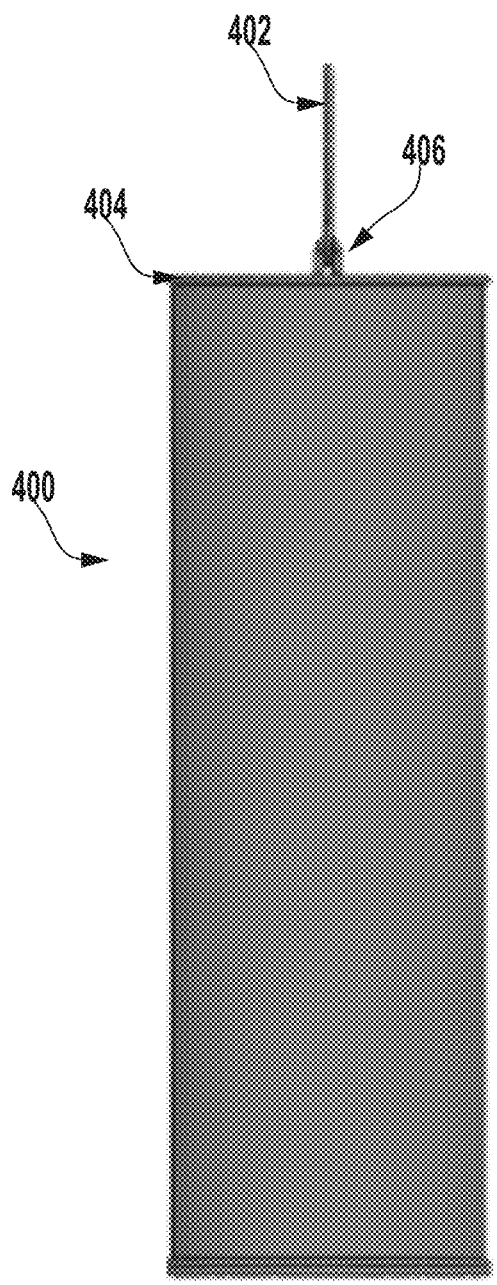
FIG. 12 a side view of the inner vessel of FIG. 4.

FIG. 12 a side view of the inner vessel of FIG. 4.

Figure 13:
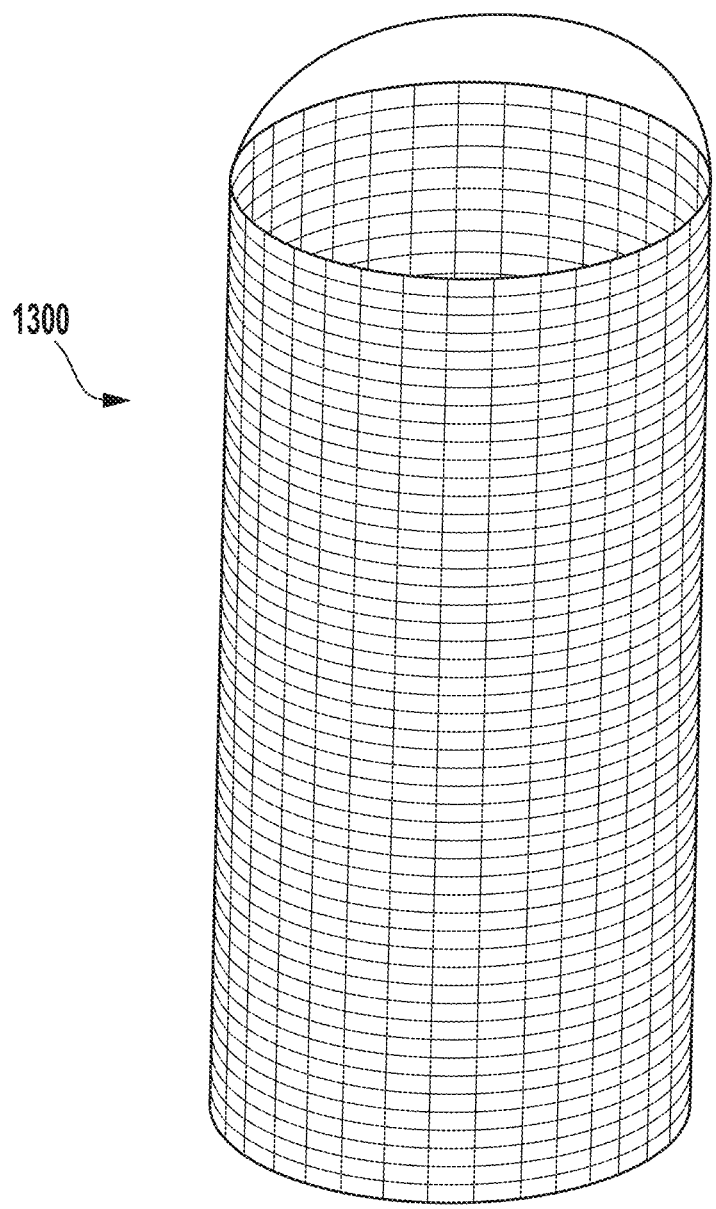
FIG. 13 a perspective view of an inner vessel of an extraction system for testing microbial contamination of tissue products, according to another example of the present disclosure.

FIG. 13 a perspective view of an inner vessel 1300 of an extraction system (e.g., the extraction system 100 of FIGS. 1-2) for testing microbial contamination of tissue products, according to another example of the present disclosure.

In this example, the inner vessel 1300 can be made of biocompatible stainless steel (e.g., 316 or 304 stainless steel), a biocompatible polycarbonate material, etc. and can allow extraction fluid (e.g., the extraction fluid 208 of FIG. 2) to flow into the inner vessel 1300 to submerge a tissue product (e.g., the tissue product 206 of FIG. 2). As an example, the inner vessel 1300 can be a stainless steel (SS) wire cloth or a SS perforated sheet that includes openings and the openings can be of various sizes such as, for example, approximately 0.69 cm or approximately 0.63 cm openings. In another example, the inner vessel 1300 can include openings of any suitable size, shape, or configuration for testing microbial contamination of tissue products.

Figure 14:
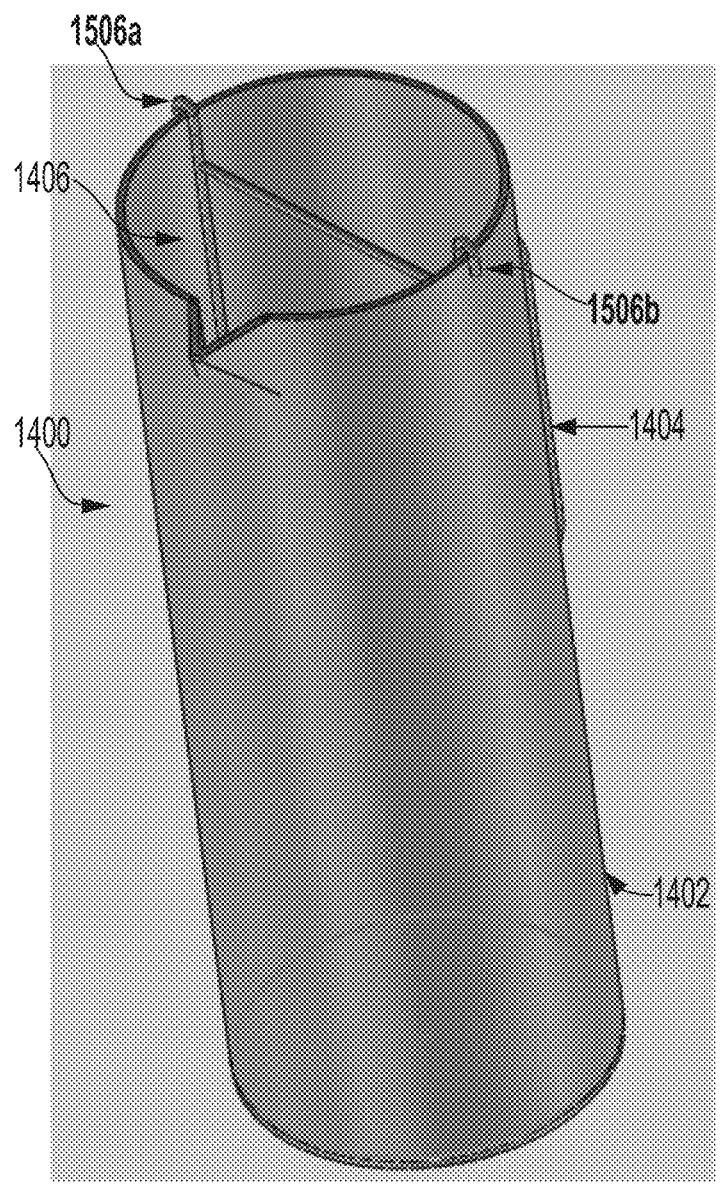
FIG. 14 is a perspective view of an extraction system for testing microbial contamination of tissue products, according to another example of the present disclosure.

FIG. 14 is a perspective view of an extraction system 1400 for testing microbial contamination of tissue products, according to another example of the present disclosure.

The extraction system 1400 can include an outer vessel 1402 that can be configured in substantially the same manner as the outer vessel of FIGS. 1-4 although it need not be. In some examples, the outer vessel 1402 can include a handle 1404.

In this example, the extraction system 1400 can include a suspension system 1406 rather than an inner vessel (e.g., instead of the inner vessel of FIGS. 1-4).

The suspension system 1406 can be positioned within the outer vessel 1402 of the extraction system 1400 and can include one or more components on which tissue (e.g., soft tissue) can be placed for testing microbial contamination of the tissue. For example, FIG. 15 a perspective view of a suspension system 1406 of the extraction system 1400 for testing microbial contamination of tissue products, according to one example of the present disclosure.

In this example, the suspension system 1406 can be positioned within an extraction system (e.g., within the outer vessel of the extraction system). The suspension system 1406 can include one or more horizontal rods 1502*a-c* or one or more vertical rods 1504*a-b*, each of which can be of any suitable size, length, shape, etc. for testing microbial contamination of tissue products. In some instances, suspension system 1406 comprises at least two vertical rods 1504*a-b* and at least one or at least two horizontal rods 1502*a-c*. As an example, each vertical rod 1504*a-b* can have a length of approximately thirteen inches. In some examples, a length of a vertical rod 1504*a-b* can be within approximately one-tenth of a centimeter from a length of the outer vessel. In another example, a length of a horizontal rod 1502*a-c* can be within a tenth of a centimeter from an internal diameter of the outer vessel. In some examples, each rod 1502*a-c* and 1504*a-b* can be made of any material for testing microbial contamination of tissue products. As an example, each rod 1502*a-c* and 1504*a-b* can be made of a biocompatible stainless steel material (e.g., 316 or 304 stainless steel), biocompatible polycarbonate material, etc.

The horizontal rods 1502*a-c* can be coupled (e.g., attached) to the vertical rods 1504*a-b* and spaced or positioned along a length of the vertical rods 1504*a-b*. For example, the horizontal rods 1502*a-c* can be spaced along the length of the vertical rods 1504*a-b* such that the horizontal rods 1502*a-c* are positioned along a length of an outer vessel of an extraction system within which the suspension system 1406 is positioned. As an example, a first horizontal rod 1502*b* can be coupled to the vertical rods 1504*a-c* at a position that is approximately at a center of an outer vessel of the extraction system within which the suspension system 1406 is positioned (e.g., the inner vessel of FIGS. 1-4). As another example, a second horizontal rod 1502*c* can be coupled to the vertical rods 1504*a-c* at a position that is above the horizontal rod 1502*b* and proximate to a first end (e.g., a top end) of the outer vessel. For instance, the horizontal rod 1502*c* can be coupled to the vertical rods 1504*a-c* at a position that is approximately one inch from the first end of the outer vessel of the extraction system within which the suspension system 1406 is positioned. As still another example, a third horizontal rod 1502a can be coupled to the vertical rods 1504a-c at a position that is below the horizontal rod 1502b and proximate to a second end (e.g., a bottom end) of the outer vessel. For instance, the horizontal rod 1502a can be coupled to the vertical rods 1504a-c at a position that is approximately 0.25 inches from the second end of the outer vessel of the extraction system within which the suspension system 1406 is positioned.

In some examples the suspension system 1406 can include one or more hooks 1506a-b, curves, or other components that can be configured for coupling the suspension system 1406 to an outer vessel of an extraction system. For example, and with reference to FIGS. 14-15, the suspension system 1406 can include hooks 1506a-b at a first end (e.g., a top end) of the suspension system 1406. The hooks 1506a-b can be configured for coupling the suspension system 1406 to a first end of the outer vessel 1402.

In some examples, the suspension system 1406 can be positioned within the outer vessel 1402 of the extraction system 1400 and coupled to the extraction system 1400 such that tissue (e.g., soft tissue such as, for example, skin, fascia, placental tissues, tendons, etc.) can be placed on, or clamped onto (e.g., via one or more fixed or moveable clamps or other fastening devices), one or more components of the suspension system 1406 (e.g., the horizontal rods 1502a-c), which can allow the extraction system 1400 to be used to detect microbial contamination of the tissue in substantially the same manner as described above.

Figure 15:
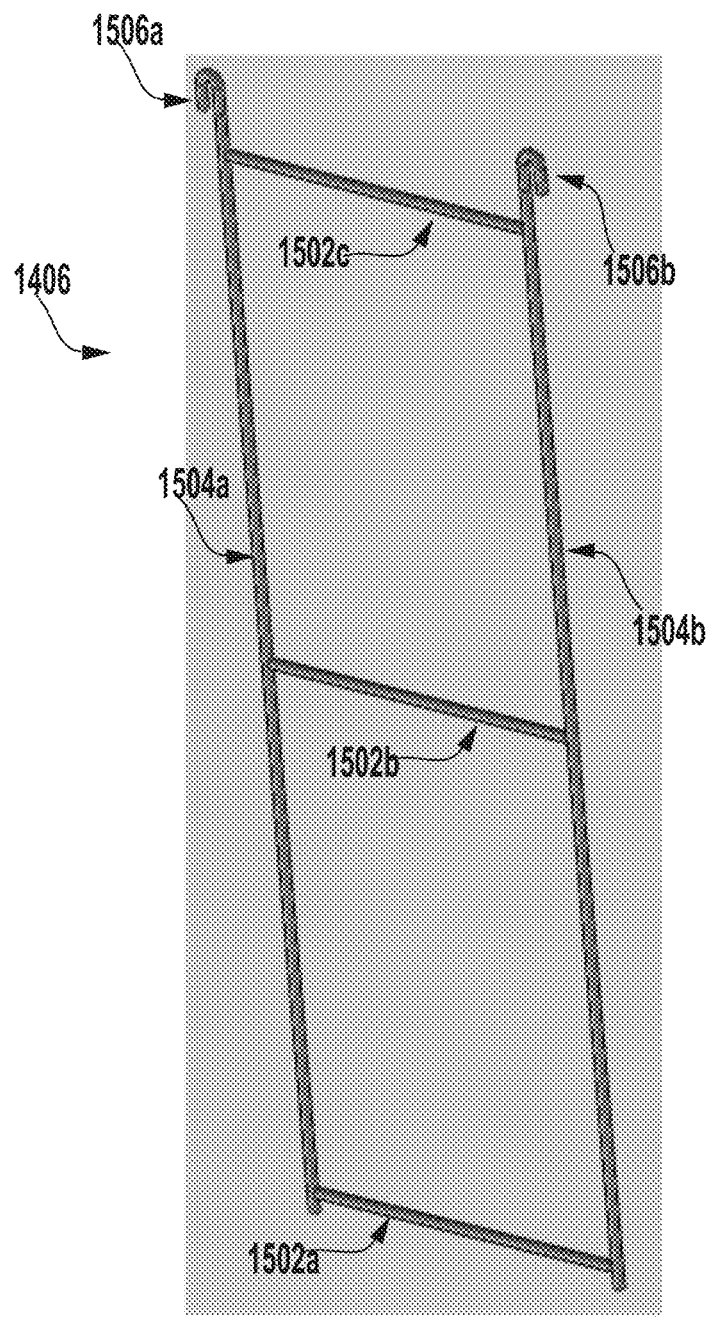
FIG. 15 a perspective view of a suspension system of an extraction system for testing microbial contamination of tissue products, according to one example of the present disclosure.

While in FIGS. 14-15, the suspension system 1406 is depicted as including various rods and one or more hooks or curves, the present disclosure is not limited to such configurations. Rather, in some embodiments, a suspension system of an extraction system can include any component for detecting microbial contamination of tissue. As an example, the suspension system can include one or more trays on which allograft, autograft, and/or xenograft products, tissue, powder, granules, fragments, etc. can be placed for detecting microbial contamination of the allograft, autograft, and/or xenograft product, tissue, or powder in substantially the same manner as described above.

Furthermore, while in some examples described above, the extraction system is described as including an inner vessel that includes a handle, the present disclosure is not limited to such configurations. Rather, in some embodiments, an inner vessel of an extraction system may not include a handle.

Figure 16:
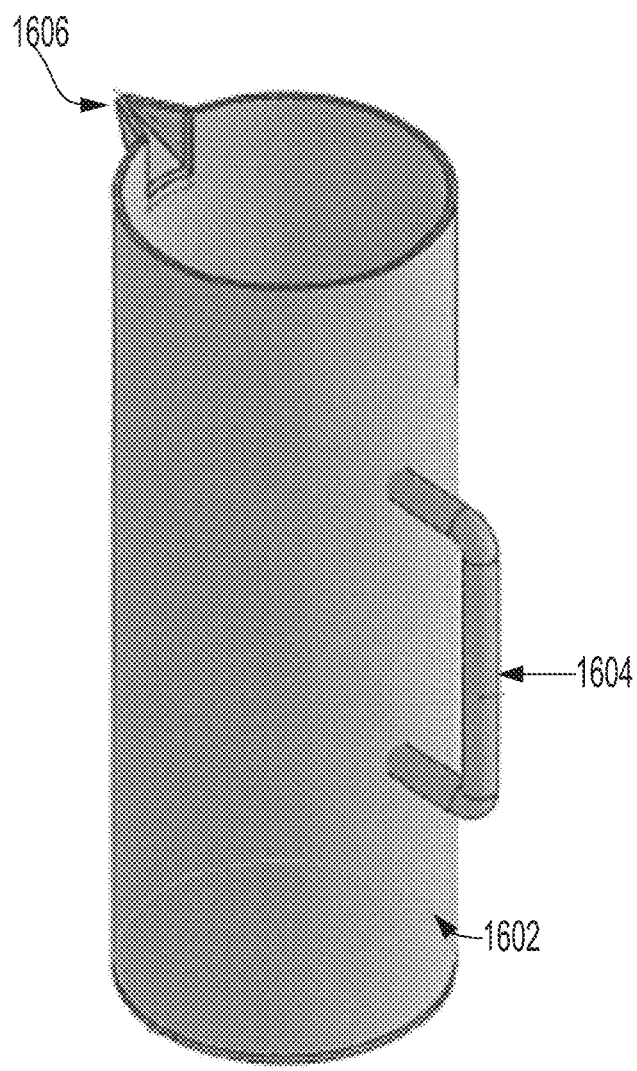
FIG. 16 is a perspective view of an outer vessel of an extraction system for testing microbial contamination of tissue products, according to another example of the present disclosure.

FIG. 16 is a perspective view of an outer vessel 1602 of an extraction system for testing microbial contamination of tissue products, according to another example of the present disclosure.

The outer vessel 1602 can be configured in substantially the same manner the outer vessel of FIGS. 1-4, although it need not be. In some examples, the outer vessel 1602 can include a handle 1604 and a first end (e.g., a top end) of the outer vessel 1602 can include a spout 1606 (e.g., a portion of the first end that extends or projects away from the first end).

Figure 17:
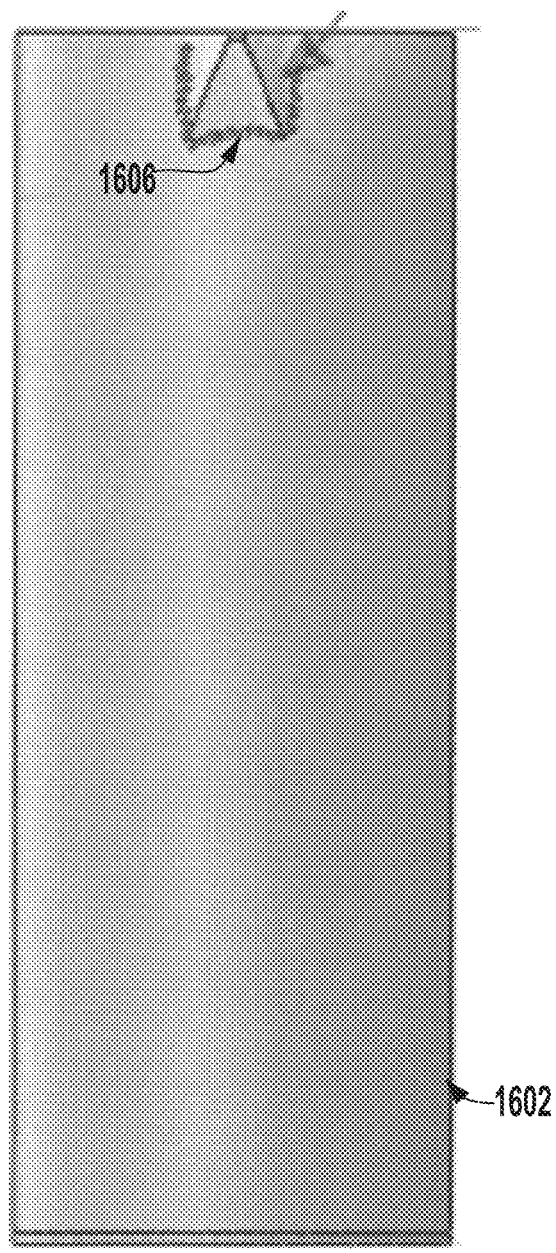
FIG. 17 is a front view of the outer vessel of FIG. 16.
Figure 18:
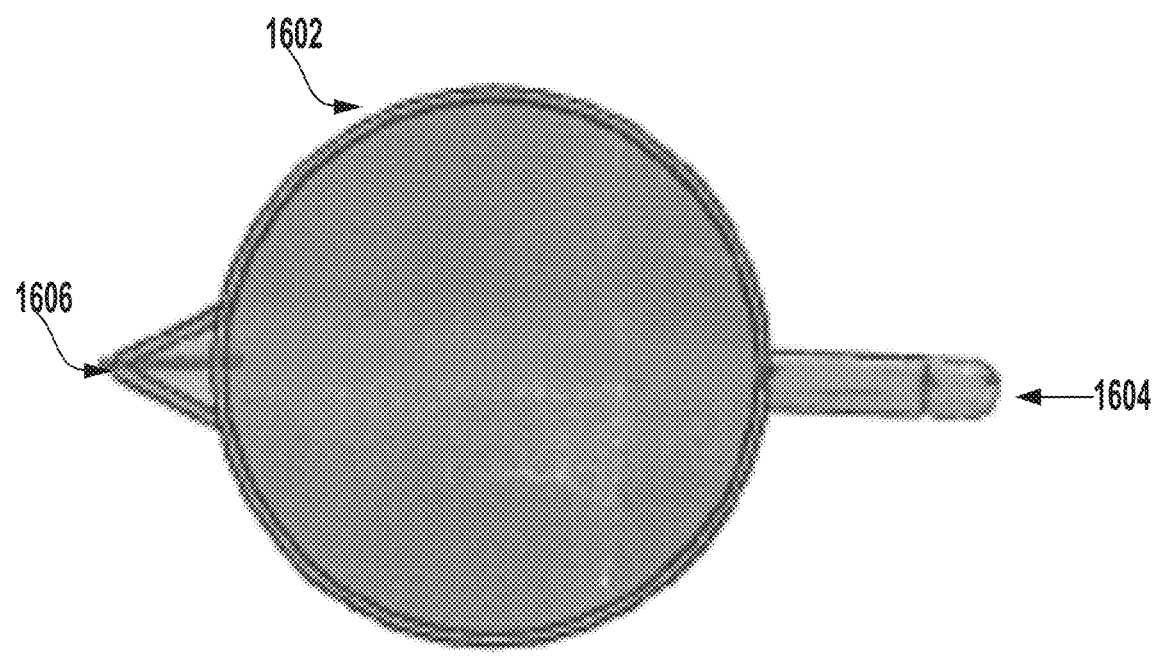
FIG. 18 is a top view of the outer vessel of FIG. 16.
Figure 19:
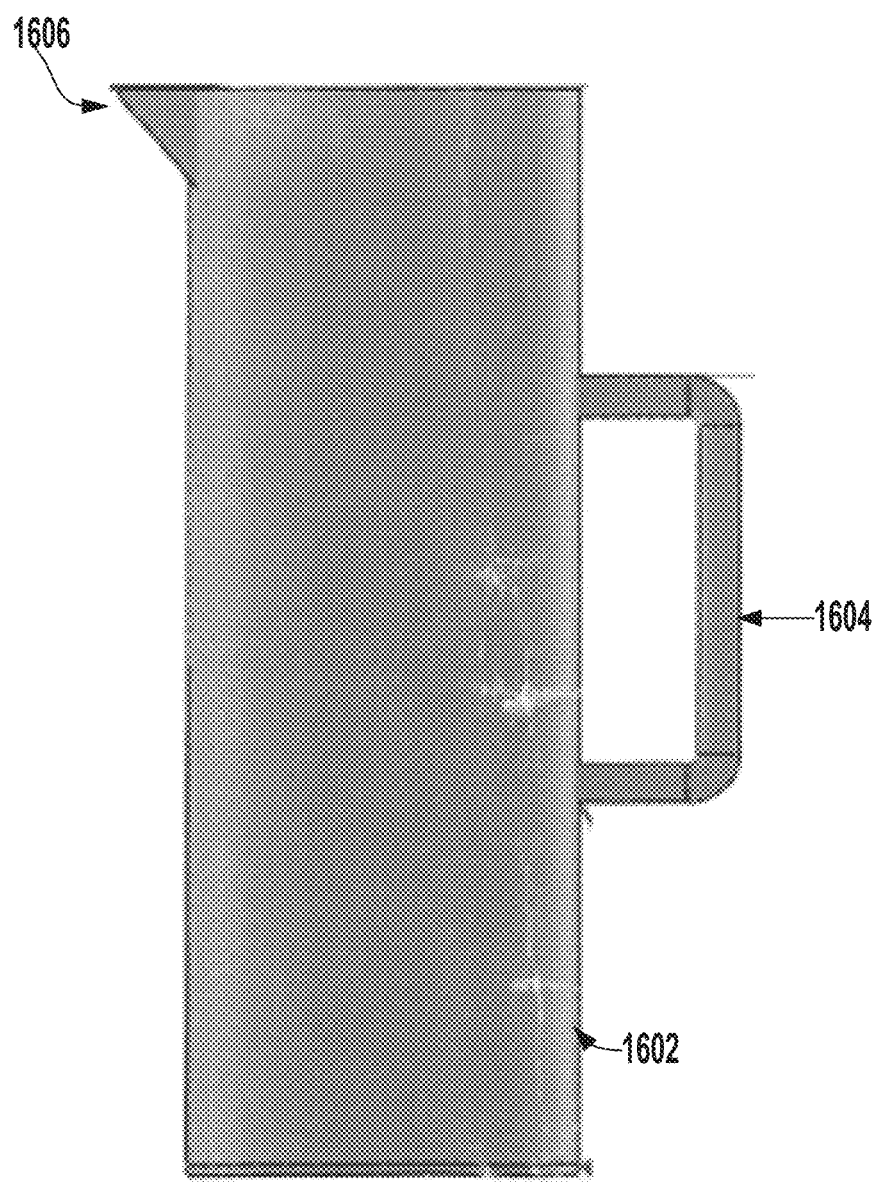
FIG. 19 is a side view of the outer vessel of FIG. 16.
Figure 20:
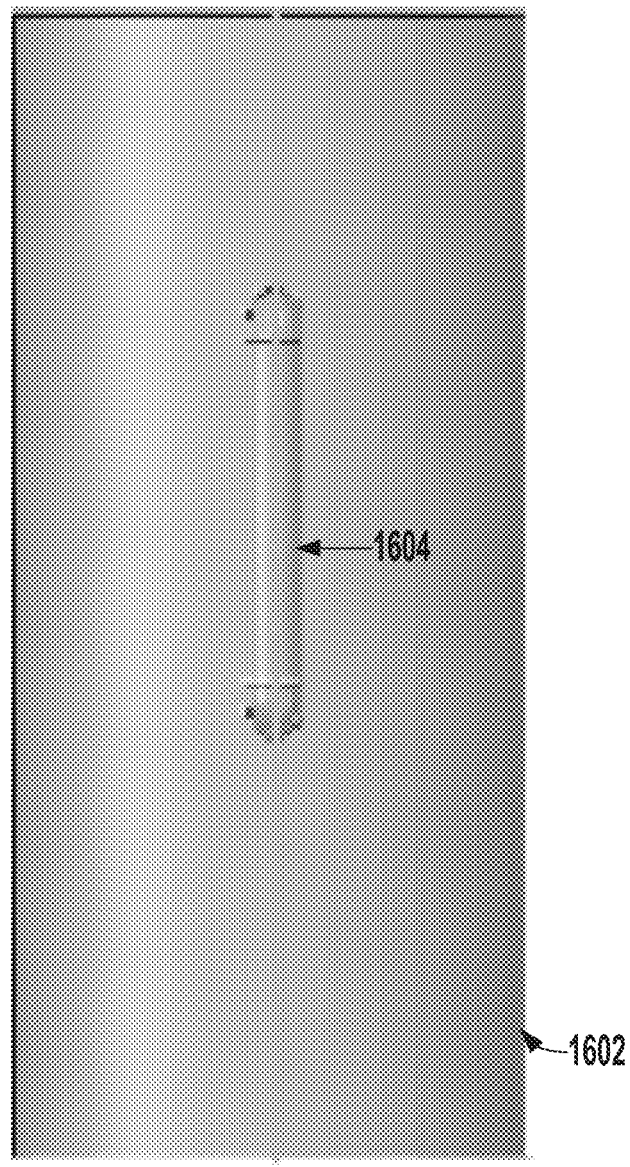
FIG. 20 is a back view of the outer vessel of FIG. 16.
Figure 21:
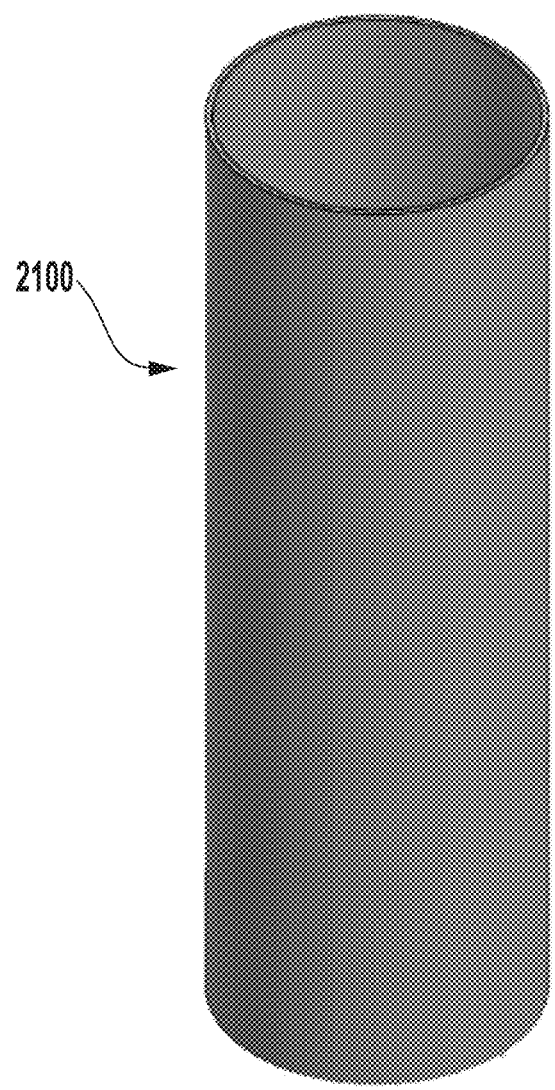
FIG. 21 is a perspective view of an inner vessel of an extraction system for testing microbial contamination of tissue products, according to another example of the present disclosure.

FIG. 17 is a front view of the outer vessel of FIG. 16.
FIG. 18 is a top view of the outer vessel of FIG. 16.
FIG. 19 is a side view of the outer vessel of the 1602 of FIG. 16.
FIG. 20 is a back view of the outer vessel of FIG. 16.
FIG. 21 is a perspective view of an inner vessel 2100 of an extraction system for testing microbial contamination of tissue products, according to another example of the present disclosure. In this example, the inner vessel 2100 may not include a handle (e.g., the handle 112 of FIG. 1).

Figure 22:
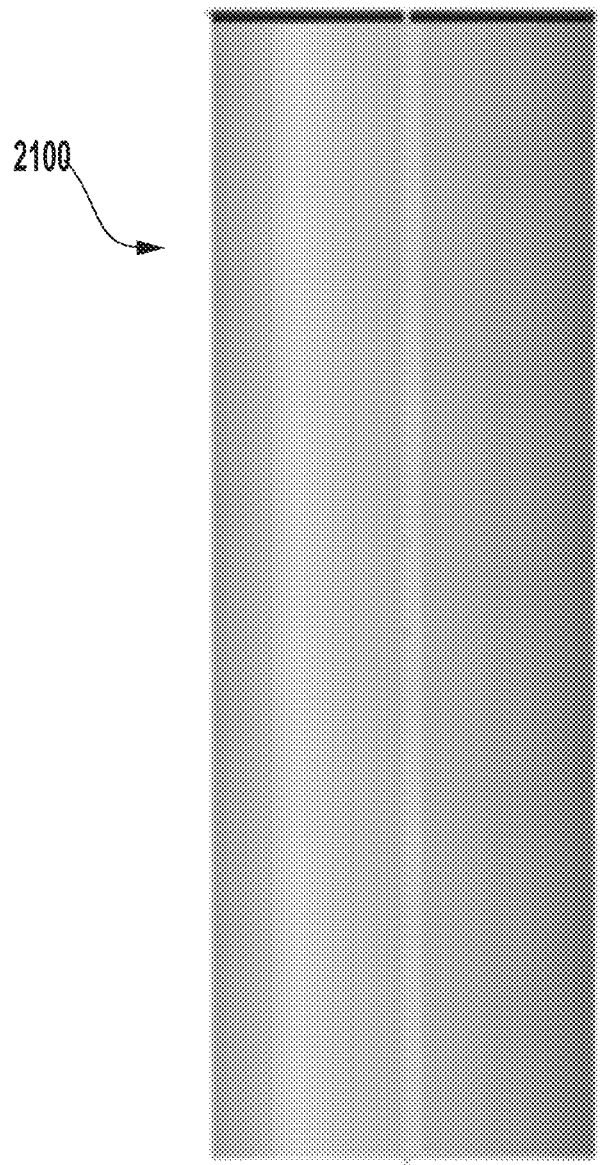
FIG. 22 is a side view of the inner vessel of FIG. 21.
Figure 23:
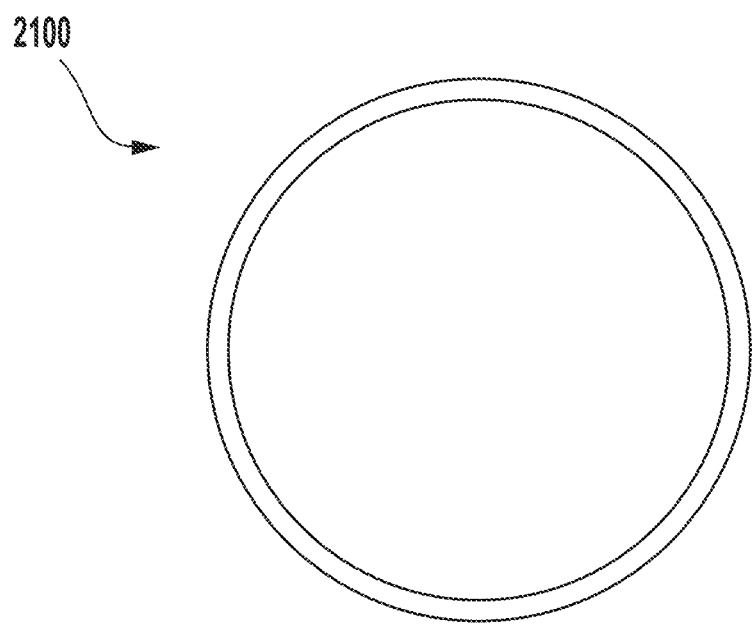
FIG. 23 is a top view of the inner vessel of FIG. 21.
Figure 24:
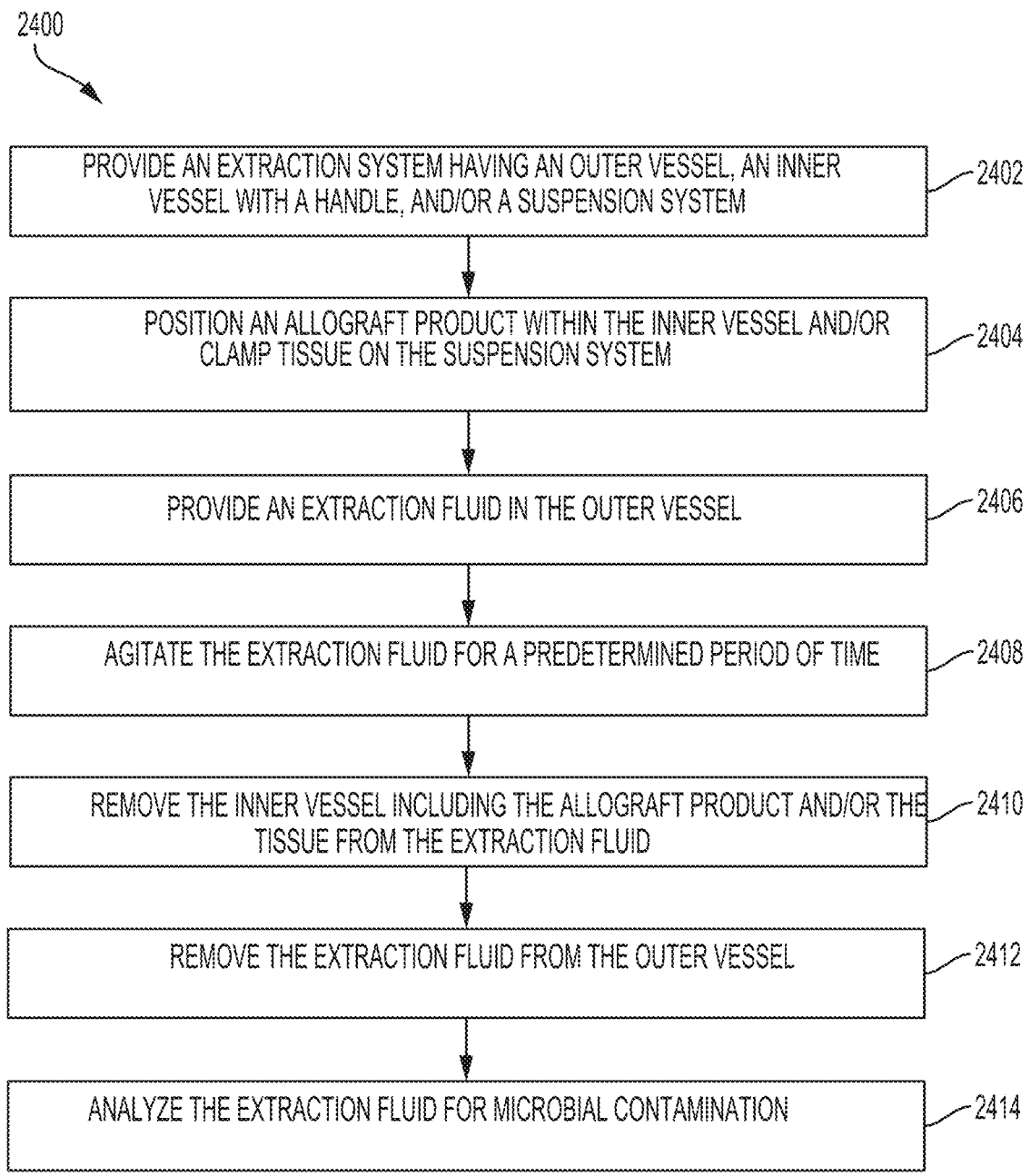
FIG. 24 is a flow chart depicting an example of a process for testing microbial contamination of tissue products, according to one example of the present disclosure.

FIG. 22 is a side view of the inner vessel 2100 of FIG. 21.
FIG. 23 is a top view of the inner vessel 2100 of FIG. 21.
FIG. 24 is a flow chart depicting an example of a process 2400 for testing microbial contamination of tissue products, according to one example of the present disclosure. Other examples can include more steps, fewer steps, or a different order of the steps shown in FIG. 24. The steps below are described with reference to the components of FIGS. 1-15, but other implementations are possible.

In block 2402, an extraction system 100 is provided. The extraction system 100 includes an outer vessel 102 and an inner vessel 104 positioned within the outer vessel 102.

The outer vessel 102 can have a height of approximately fourteen inches, an inner diameter of approximately four inches (e.g., 4.60 inches), and an outer diameter of approximately five inches. In some examples, the outer vessel 102 can have a height between approximately four inches and approximately thirty inches. In still another example, the outer vessel 102 can have a height that is greater than thirty centimeters. As an example, the outer vessel 102 can have a height of thirty-three centimeters. In still another example, the outer vessel 102 can have an inner diameter between approximately twelve centimeters and approximately eleven centimeters. As an example, the outer vessel 102 can have an inner diameter between approximately 11.351 centimeters and approximately 11.509 centimeters. In some examples, the outer vessel 102 can have an average diameter between approximately two inches and approximately eight inches.

In some instances, the outer vessel 102 can have a first end (e.g., a top end) and the first end of the outer vessel 102 can include a spout 106 (e.g., a portion of the first end that extends away from the first end). In some examples, the outer vessel 102 can also include a handle, a flange, or a lid, each of which can be coupled to the outer vessel 102. In some instances, the flange may be coupled (e.g., attached or connected) to a second end (e.g., bottom end) of the outer vessel 102 and can extend away from the second end (e.g., extend approximately one inch away from a circumference of the second end), which can allow the flange to stabilize the extraction system 100 and reduce vibration during sonication operations.

In some examples, the inner vessel 104 of the extraction system 100 can be a stainless steel perforated sheet. The inner vessel 104 can have a height of approximately thirteen inches and a diameter of approximately four inches (e.g., 4.2 inches). In some examples, a height, size, or thickness of the inner vessel 104 can be proportional to a height, size, or thickness of the outer vessel 102. In some instances, a handle 112 can be coupled to an end (e.g., a top end) of the inner vessel 104.

The extraction system 100 can include a suspension system 1406, which can be positioned within the outer vessel 102 and the suspension system 1406 can include one or more components on which tissue (e.g., soft tissue) can be placed for testing microbial contamination of the tissue.

In some examples, the extraction system 100 can include the suspension system 1406 instead of the inner vessel 104. In some examples, the extraction system 100 can include the suspension system 1406 positioned within the inner vessel 104

In block 2404, a tissue product 206 is positioned within the inner vessel 104. For example, a head of a femur or other femoral shaft is positioned within the inner vessel 104. In some examples, if the extraction system 100 includes the suspension system 1406 in block 2404, tissue can be clamped on the suspension system 1406. For example, soft tissue such as, for example, skin, fascia, placental tissues, tendons, etc. is placed on, or clamped onto (e.g., via one or more fixed or moveable clamps or fastening devices), one or more components of the suspension system 1406 (e.g., horizontal rods 1502*a-c* of the suspension system 1406).

In block 2406, an extraction fluid 208 is provided in the outer vessel 102. For example, water or other suitable extraction fluid 208 can be dispersed into the outer vessel 102.

In some examples, the tissue product 206 (the tissue) and the extraction fluid 208 can be positioned within the outer vessel 102 such that the tissue product 206 is submerged within the extraction fluid 208. As an example, the inner vessel 104 is a stainless steel perforated sheet or wire cloth that can allow the extraction fluid 208 to flow into the inner vessel 104 to submerge the tissue product 206. In some examples, if the extraction system 100 includes the suspension system 1406, in block 2406, the tissue and the extraction fluid 208 can be positioned within the outer vessel 102 or, if the inner vessel 104 is present, within the inner vessel 104, such that the tissue is submerged within the extraction fluid 208.

Figure 25:
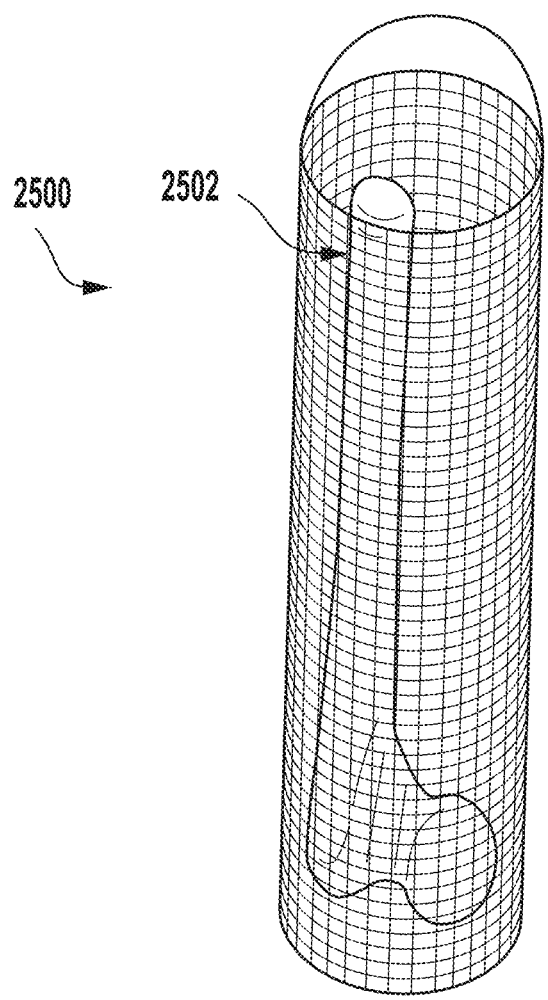
FIG. 25 is a side view of an extraction system for testing microbial contamination of tissue products, according to another example of the present disclosure.

For example, FIG. 25 is a side view of an extraction system 2500 for testing microbial contamination of tissue products, according to another example of the present disclosure.

In the example depicted in FIG. 25, a tissue product 2502 (a portion of femoral bone) positioned within the extraction system 2500 (e.g., within an inner vessel of the extraction system 2500) is submerged by extraction fluid positioned within the extraction system 2500.

Returning to FIG. 24, in block 2408, the extraction fluid 208 is agitated for a predetermined amount of time.

For example, the extraction fluid 208, along with the tissue product 206 and the tissue on the suspension system 1406, can be agitated (e.g., sonicated) for a period of time to release microorganisms from the tissue product 206 and the tissue into the extraction fluid 208. In one example, a tank of a sonicator is filled with water (such as between about 2-4 L). The extraction system 2500 (e.g., an outer vessel and any other interior components) containing the tissue and extraction fluid is placed into the tank. Ultrasonic motors of the sonicator proximate the tank are engaged to produce ultrasonic energy that propagates through the extraction system 2500. The ultrasonic energy is sufficient to "shake loose" microorganisms from the tissue surface, but is not so strong that it kills the microbes.

In block 2410, the inner vessel 104 including the tissue product 206 and the tissue are removed from the extraction fluid 208 and outer vessel 102.

In block 2412, the extraction fluid 208 is removed from the outer vessel 102. For example, the extraction fluid 208 that contains microorganisms released from the tissue can be removed from the outer vessel 102 (e.g., via a spout 106 of the outer vessel 102 and using a handle 108 of the outer vessel 102).

In block 2414, the extraction fluid 208 is analyzed for microbial contamination (e.g., cultured to determine if microbial contamination is present).

While in this example, the inner vessel 104 is removed from within the outer vessel 102 after agitating the extraction system 100, the present disclosure is not limited to such configurations. Rather, in some examples, the inner vessel 104 can be removed while the extraction fluid 208 and the extraction system 100 is being agitated and the extraction fluid 208 can subsequently be analyzed for microbial contamination in substantially the same manner as described above.

Figure 26:
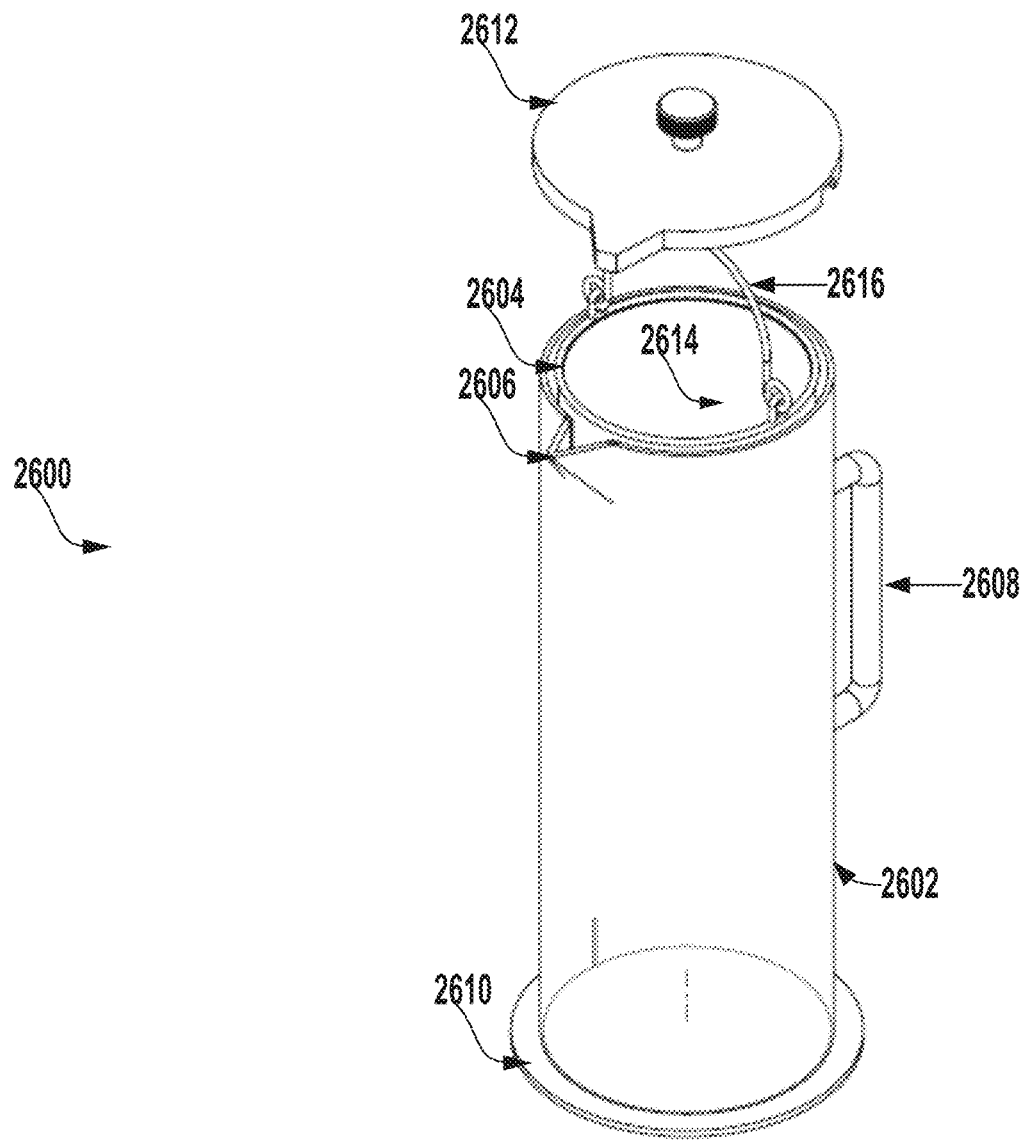
FIG. 26 is a perspective view of an extraction system for testing microbial contamination of tissue products, according to another example of the present disclosure.

FIG. 26 is a perspective view of an extraction system 2600 for testing microbial contamination of tissue products, according to another example of the present disclosure.

The extraction system 2600 can include an outer vessel 2602 and an inner vessel 2604 positioned within the outer vessel 2602. The inner vessel 2604 and outer vessel 2602 can each be made of a biocompatible stainless steel material and can each have a circular cross-section (e.g., the inner and outer vessels can each have a cylindrical shape) formed from a single side wall. In other embodiments, multiple curved and/or straight side walls may be joined to form an inner vessel 2604 and/or outer vessel 2602 having a non-circular cross-section.

In some examples, the outer vessel 2602 can have a first end (e.g., a top end) and a second end (e.g., a bottom end). The first end of the outer vessel 2602 can include a spout 2606 (e.g., a portion of the first end that extends away from the first end). In some examples, the outer vessel 2602 can also include a handle 2608, a flange 2610, or a lid (e.g., cap) 2612, each of which can be coupled (e.g., attached or connected) to the outer vessel 2602. In some instances, the flange 2610 may be coupled to the second end of the outer vessel 2602 and can extend away from the second end (e.g., extend approximately one inch away from a circumference of the second end), which can allow the flange 2610 to stabilize the extraction system 2600 during sonication operations and reduce vibration during such sonication operations.

Figure 27:
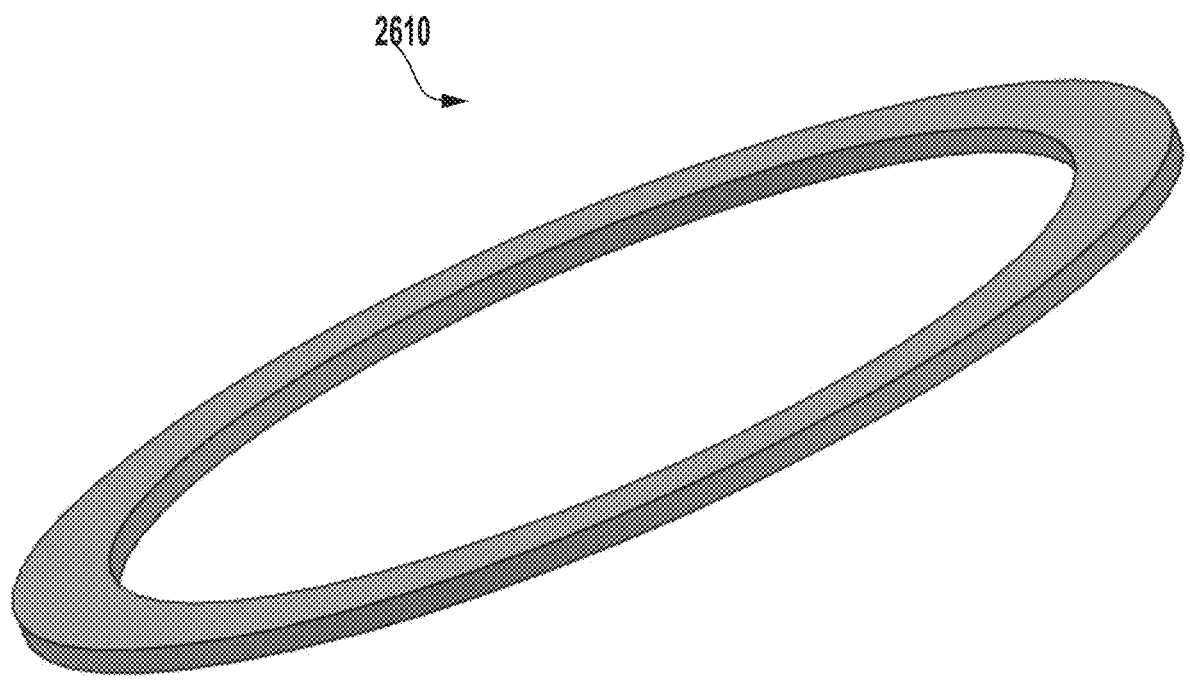
FIG. 27 a perspective view of a flange of an extraction system for testing microbial contamination of tissue products, according to one example of the present disclosure.

For example, FIG. 27 is a perspective view of a flange 2610 of an extraction system for testing microbial contamination of tissue products, according to one example of the present disclosure. In some instances, the flange 2610 may be a ring shape with a void defined in the center, the void defined to fit the outer diameter of the outer vessel 2602. In some examples, the flange 2610 can be a disc that can be coupled to an end of an extraction system (e.g., a bottom of the extraction system). In this example, the disc can have a diameter that is greater than a diameter of an outer vessel 2602 of the extraction system such that the disc extends beyond a perimeter of the outer vessel 2602 to form a flange. While circular shapes are shown for flange 2610, this component can be configured to match the shape of the outer vessel 2602 of the extraction system.

Figure 28:
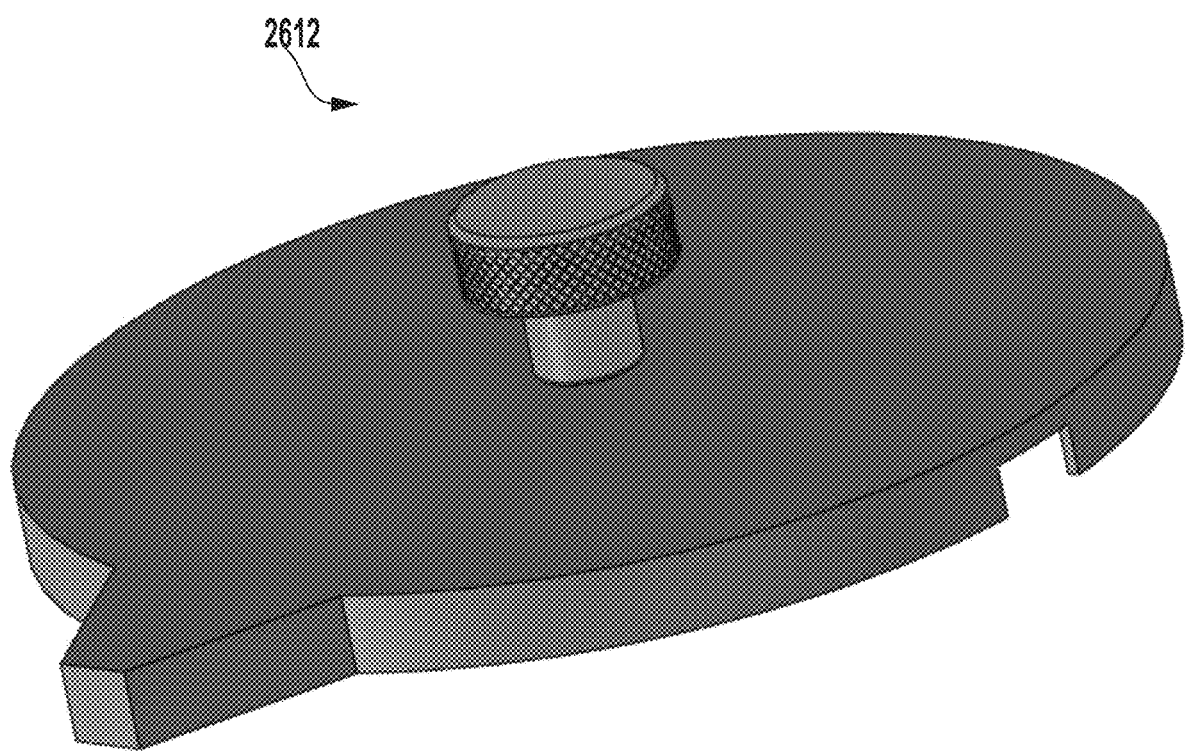
FIG. 28 a perspective view of a cap or lid of an extraction system for testing microbial contamination of tissue products, according to one example of the present disclosure.

FIG. 28 a perspective view of a cap or lid 2612 of an extraction system for testing microbial contamination of tissue products, according to one example of the present disclosure. In some examples, the cap or lid 2612 can be configured such that the lid 2612 can be coupled to a first end (e.g., top end) of an outer vessel of an extraction system (e.g., the outer vessel 2602 of FIG. 26) to seal the extraction system (e.g., seal the extraction system 2600).

Returning to FIG. 26, the inner vessel 2604 can include an opening 2614 at a first end (e.g., a top end) of the inner vessel 2604, which can allow a tissue product (e.g., a head of a femur or other femoral shafts) to be positioned within the inner vessel 2604. In some examples, the inner vessel 2604 can include a handle 2616 that is coupled to the inner vessel 2604.

Figure 29:
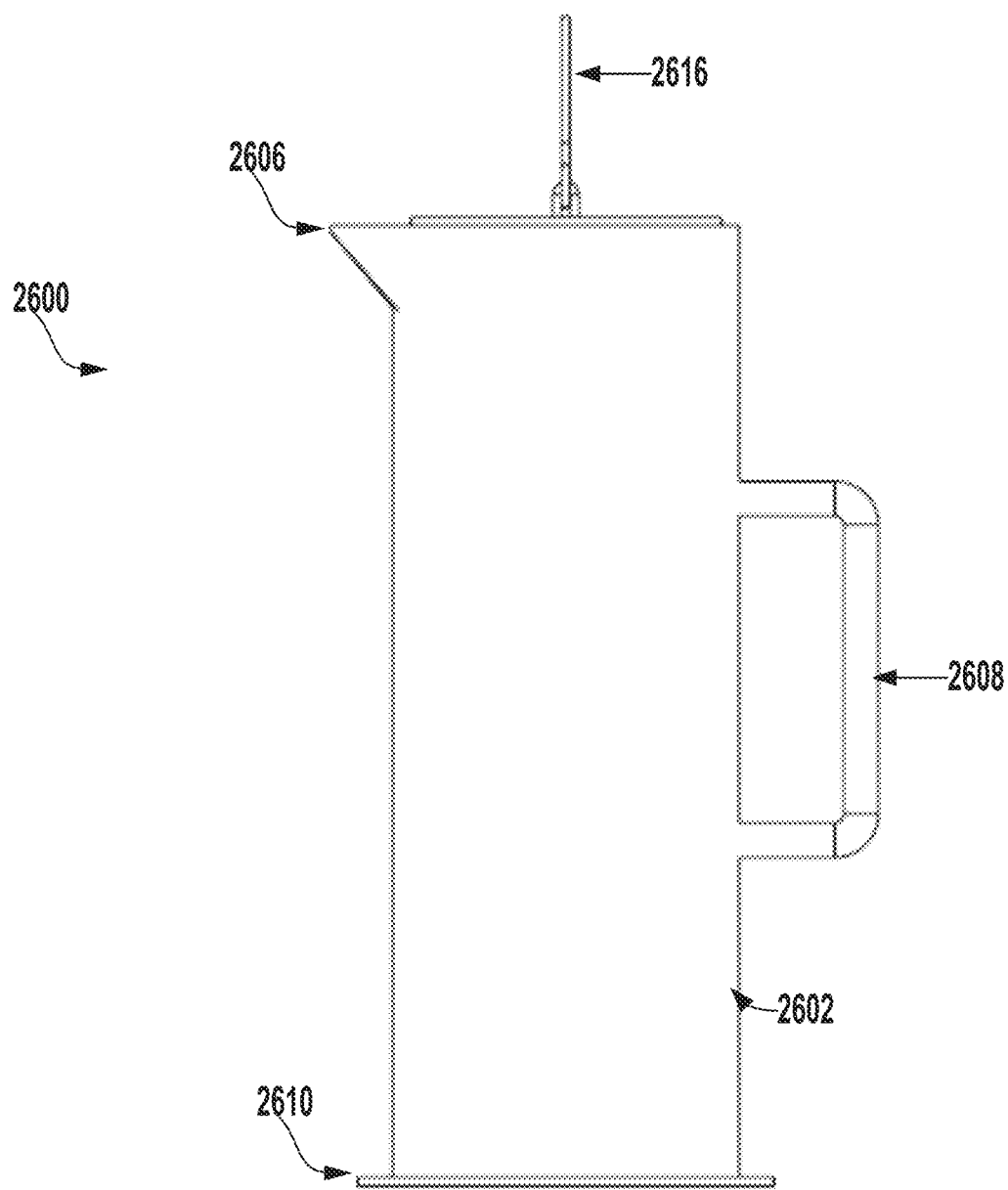
FIG. 29 is a side view of the extraction system of FIG. 26.

FIG. 29 is a side view of the extraction system of FIG. 26.

Figure 30:
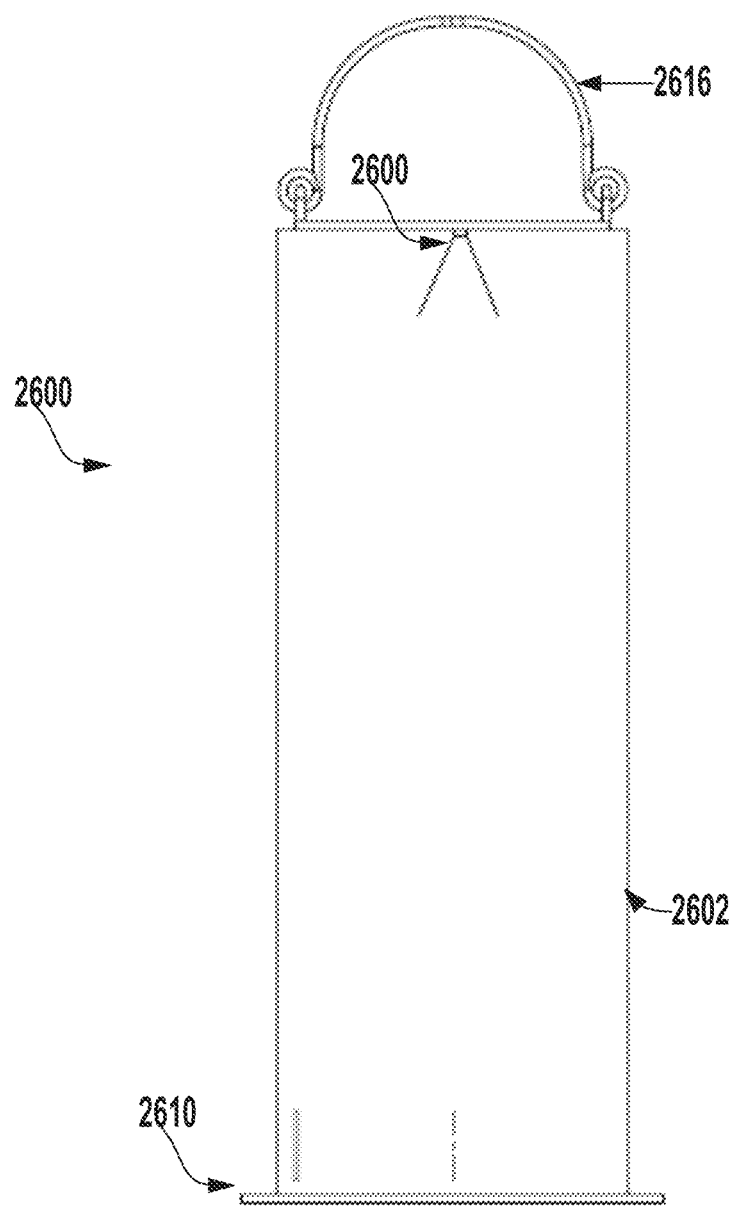
FIG. 30 is a front view of the extraction system of FIG. 26.

FIG. 30 is a front view of the extraction system of FIG. 26.

Figure 31:
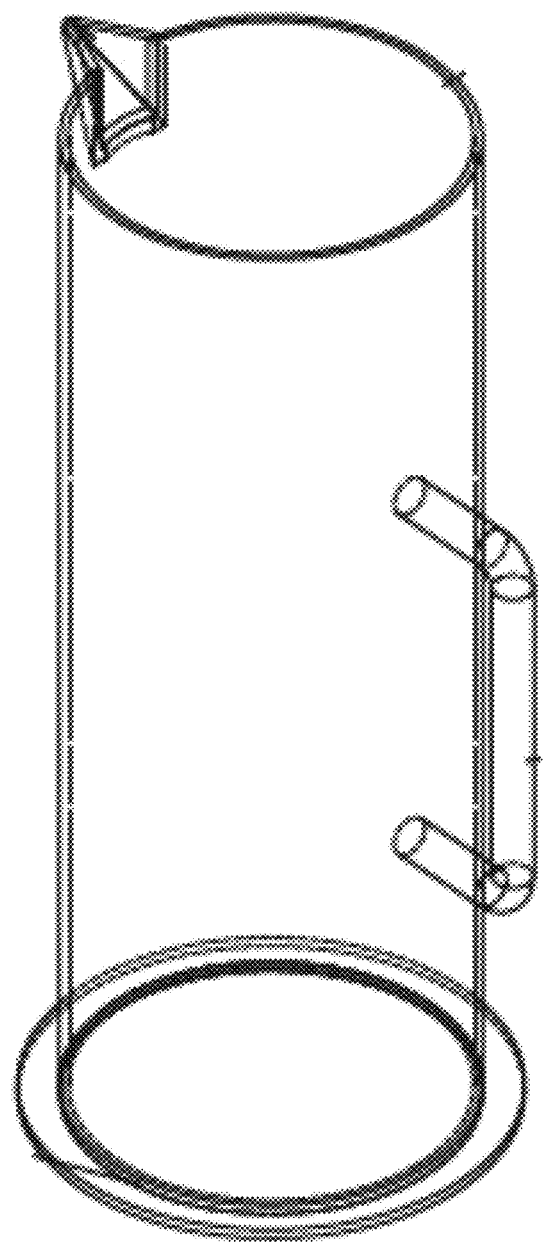
FIG. 31 is a perspective view of an outer vessel of an extraction system for testing microbial contamination of tissue products, according to another example of the present disclosure.

FIG. 31 is a perspective view of an outer vessel of an extraction system for testing microbial contamination of tissue products, according to another example of the present disclosure.

Example

Testing was conducted to determine the effectiveness of the extraction system of the present disclosure. A microbial culturing method (extraction culture) was used in which tissue is placed into a fluid bath within an extraction vessel (such as those described herein). In such microbial culturing processes, tissue is then exposed to sonic energy via an ultrasonicator. The delivered energy from the sonicator has the capability to liberate microorganisms from the tissue into the fluid which can then be assayed to determine the presence of microbial contamination on the tissue.

To evaluate the effectiveness of the new extraction vessel design, testing was performed to ensure energy was being propagated through a prototype vessel. Energy levels within the prototype vessel were measured and compared to measured energy levels within a conventional extraction vessel. Testing parameters included extraction vessel water level and position of an energy meter within the vessel.

Prototype Description

The prototype extraction vessel was a stainless steel outer extraction vessel having a handle and spout, very much like is shown in FIG. 1. The dimensions of the prototype vessel were approximately 13.5 inches tall by 5 inches outer diameter and 4.75 inches inner diameter.

A Branson 5800 Ultrasonicator was prepared by filling a tank of the sonicator with 2 L of water. The extraction vessel was inserted into the tank. A PPB Megasonics pb-500 Ultrasonic Energy Meter was inserted into the vessel. The depth of the energy meter was controlled by affixing a measuring end of the energy meter to the desired spot on a ruler with rubber bands. The ruler and energy meter were then lowered into the extraction vessel until the ruler reached the bottom of the extraction vessel. The extraction vessel was filled with varying depths of water. To take measurements, the sonicator was activated at an output of 160 W at 40 kHz, the energy meter was placed into position, the energy meter was activated, and an average energy output (in W/gal) was measured over a 1-minute span. This procedure was followed for both a conventional extraction vessel and a prototype extraction vessel based on the present disclosure.

Table 1 illustrates energy within each vessel as measured at center-bottom (½ inch from base) of vessel with varying water levels. Average energy reading is shown in W/gal.

TABLE 1

| Vessel | 1 L water | 2 L water | 3 L water | 4 L water |
| --- | --- | --- | --- | --- |
| #1 conventional | 5 | 6 | 4 | 7 |
| #2 prototype | 7 | 8 | 11 | 8 |

Table 2 illustrates energy in W/gal as measured at edge-bottom (½ inch from base) of vessel with varying water levels.

TABLE 2

| Vessel | 1 L water | 2 L water | 3 L water | 4 L water |
| --- | --- | --- | --- | --- |
| #1 conventional | 5 | 3 | 2 | 3 |
| #2 prototype | 4 | 11 | 4 | 7 |

Table 3 illustrates energy in W/gal as measured at center of vessel at varying depths and fixed water level of 4 L.

TABLE 3

| Vessel | 1 inch from base | 2 inches from base | 3 inches from base | 4 inches from base |
| --- | --- | --- | --- | --- |
| #1 conventional | 12 | 19 | 16 | 13 |
| #2 prototype | 19 | 15 | 14 | 19 |

These results demonstrate that energy effectively propagates through the prototype vessel and that energy levels in the prototype vessel were comparable to those found in conventional vessels.

The foregoing description of certain examples, including illustrated examples, has been presented only for the purpose of illustration and description and is not intended to be exhaustive or to limit the disclosure to the precise forms disclosed.

Numerous modifications, adaptations, and uses thereof will be apparent to those skilled in the art without departing from the scope of the disclosure.

Also, the words "comprise", "comprising", "contains", "containing", "include", "including", and "includes", when used in this specification and in the following claims, are intended to specify the presence of stated features, integers, components, or steps, but they do not preclude the presence or addition of one or more other features, integers, components, steps, acts, or groups.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About" and/or "approximately" as used herein when referring to a measurable value such as an amount, a temporal duration, and the like, encompasses variations of ±20% or ±10%, ±5%, or +0.1% from the specified value, as such variations are appropriate to in the context of the systems, devices, circuits, methods, and other implementations described herein. "Substantially" as used herein when referring to a measurable value such as an amount, a temporal duration, a physical attribute (such as frequency), and the like, also encompasses variations of ±20% or ±10%, ±5%, or +0.1% from the specified value, as such variations are appropriate to in the context of the systems, devices, circuits, methods, and other implementations described herein.

As used herein, including in the claims, "and" as used in a list of items prefaced by "at least one of" or "one or more of" indicates that any combination of the listed items may be used. For example, a list of "at least one of A, B, and C" includes any of the combinations A or B or C or AB or AC or BC and/or ABC (i.e., A and B and C). Furthermore, to the extent more than one occurrence or use of the items A, B, or C is possible, multiple uses of A, B, and/or C may form part of the contemplated combinations. For example, a list of "at least one of A, B, and C" may also include AA, AAB, AAA, BB, etc.

What is claimed is:

1. An extraction system for testing microbial contamination, the system comprising:
    a biocompatible outer vessel comprising a side wall; and
    a biocompatible suspension system that is positionable within an interior of the biocompatible outer vessel, the biocompatible suspension system comprising:
        a horizontal member on which a tissue sample may be supported; and
        a securement mechanism that is engagable with the side wall of the biocompatible outer vessel to maintain the suspension system at a desired position within the biocompatible outer vessel.

2. The extraction system of claim 1, wherein:
    the securement mechanism comprises at least one hook that is configured to engage a top end of the side wall.

3. The extraction system of claim 1, wherein:
the biocompatible suspension system comprises at least one vertical member that is coupled with the horizontal member and the securement mechanism.

4. The extraction system of claim 1, wherein:
the biocompatible suspension system comprises a clamp that is coupled with the horizontal member, the clamp being configured to secure the tissue sample to the biocompatible suspension system.

5. The extraction system of claim 4, wherein:
the clamp is moveable along a length of the horizontal member.

6. The extraction system of claim 1, wherein:
the biocompatible outer vessel has a thickness of between about 0.5 and 3 millimeters.

7. The extraction system of claim 1, wherein:
the biocompatible outer vessel comprises at least one of a spout, a flange, or a handle.

8. An extraction system for testing microbial contamination, the system comprising:
a biocompatible outer vessel; and
a biocompatible suspension system positionable within the biocompatible outer vessel, wherein soft tissue is positionable on the biocompatible suspension system and wherein the extraction system is configured to receive a tissue sample having a size of at least thirty centimeters, wherein the biocompatible suspension system comprises a curved portion that is configured to secure the biocompatible suspension system to a top end of the biocompatible outer vessel.

9. The extraction system of claim 8, further comprising a biocompatible inner vessel positionable within the biocompatible outer vessel, the biocompatible inner vessel having a height of approximately thirteen inches and a diameter of approximately four inches, wherein the biocompatible inner vessel comprises a handle coupled to the biocompatible inner vessel.

10. The extraction system of claim 8, wherein:
the biocompatible outer vessel has a height of between about four inches and thirty inches.

11. The extraction system of claim 8, wherein:
the biocompatible outer vessel comprises at least one of a spout, a flange, or a handle.

12. The extraction system of claim 8, wherein:
the biocompatible outer vessel has a diameter of between approximately 2 inches and 8 inches.

13. The extraction system of claim 8, wherein:
the biocompatible suspension system comprises:
a first vertical member;
a second vertical member; and
a horizontal member that extends between and couples with the first vertical member and the second vertical member, the horizontal member being configured to support the tissue sample.

14. The extraction system of claim 9, wherein:
the biocompatible inner vessel comprises a perforated sheet.

15. A method of using an extraction system, comprising:
securing a tissue sample to a horizontal member of a biocompatible suspension system;
submerging at least a portion of the tissue sample in an extraction fluid provided within an interior of a biocompatible outer vessel;
agitating the extraction fluid for a predetermined period of time to release microorganism from the tissue sample;
removing the extraction fluid from the biocompatible outer vessel; and
analyzing the extraction fluid for the presence of microbes.

16. The method of using an extraction system of claim 15, further comprising:
removing the horizontal member of the biocompatible suspension system and the tissue sample from the biocompatible outer vessel prior to removing the extraction fluid.

17. The method of using an extraction system of claim 15, wherein:
the extraction fluid is agitated using a sonicator.

18. The method of using an extraction system of claim 15, wherein:
securing the tissue sample to the horizontal member comprises clamping the tissue sample to the horizontal member using at least one clamp.

19. The method of using an extraction system of claim 15, wherein:
the extraction fluid is removed from the biocompatible outer vessel while the extraction fluid is being agitated.

20. The method of using an extraction system of claim 15, wherein:
submerging the at least a portion of the tissue sample in the extraction fluid comprises coupling a securement mechanism of the biocompatible suspension system to a top end of the biocompatible outer vessel.

* * * * *